United States Patent
Chobotov et al.

(10) Patent No.: US 6,776,604 B1
(45) Date of Patent: Aug. 17, 2004

(54) METHOD AND APPARATUS FOR SHAPE FORMING ENDOVASCULAR GRAFT MATERIAL

(75) Inventors: Michael V. Chobotov, Santa Rosa, CA (US); Patrick Stephens, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 100 days.

(21) Appl. No.: 10/029,570

(22) Filed: Dec. 20, 2001

(51) Int. Cl.[7] .......................... B29C 33/42; B29C 49/48

(52) U.S. Cl. ...................................... 425/522; 425/392

(58) Field of Search .................................. 264/505, 506, 264/507; 425/522, 392, 387.1, DIG. 55

(56) References Cited

U.S. PATENT DOCUMENTS

| | | | |
|---|---|---|---|
| 1,324,850 A | * 12/1919 | Roberts ....................... | 156/251 |
| 2,372,917 A | * 4/1945 | Tuttle ............................. | 72/62 |
| 2,983,961 A | * 5/1961 | Titterton et al. ............. | 264/506 |
| 4,049,762 A | * 9/1977 | Martino et al. ............. | 264/531 |
| 4,201,144 A | 5/1980 | Manabe et al. | |
| 4,218,420 A | * 8/1980 | Jacob et al. ................. | 264/570 |
| 4,229,838 A | 10/1980 | Mano | |
| 4,319,872 A | * 3/1982 | Lupke et al. ................ | 425/532 |
| 4,386,566 A | 6/1983 | Moss | |
| 4,731,073 A | 3/1988 | Robinson | |
| 5,197,976 A | 3/1993 | Herweck et al. | |
| 5,447,152 A | 9/1995 | Kohsai et al. | |
| 5,476,506 A | 12/1995 | Lunn | |
| 5,522,881 A | 6/1996 | Lentz | |
| 5,527,353 A | 6/1996 | Schmitt | |
| 5,556,414 A | 9/1996 | Turi | |
| 5,556,426 A | 9/1996 | Popadiuk et al. | |
| 5,607,478 A | 3/1997 | Lentz et al. | |
| 5,609,624 A | 3/1997 | Kalis | |
| 5,628,782 A | 5/1997 | Myers et al. | |
| 5,628,786 A | * 5/1997 | Banas et al. ................ | 623/1.13 |

(List continued on next page.)

FOREIGN PATENT DOCUMENTS

| | | |
|---|---|---|
| EP | 821648 | 9/2001 |
| EP | 877582 | 10/2002 |
| EP | 1148843 | 4/2003 |
| WO | 95/05277 | 2/1995 |
| WO | 96/33066 | 10/1996 |
| WO | 97/27820 | 8/1997 |
| WO | 97/32714 | 9/1997 |
| WO | 98/38947 | 9/1998 |
| WO | 99/00073 | 1/1999 |
| WO | 00/42947 | 7/2000 |
| WO | 00/45741 | 8/2000 |
| WO | 01/01886 | 1/2001 |
| WO | 01/01887 | 1/2001 |
| WO | 01/15633 | 3/2001 |
| WO | 01/28456 | 4/2001 |
| WO | 01/52771 | 7/2001 |
| WO | 02/100454 | 12/2002 |
| WO | 03/003946 | 1/2003 |

OTHER PUBLICATIONS

Gunter Mennig, Mold–Making Handbook, 1998, Hanser/Gardner Publications, Inc, 2nd edition, pp. 252–253.*

Primary Examiner—Robert B. Davis
(74) Attorney, Agent, or Firm—Townsend and Townsend and Crew LLP

(57) ABSTRACT

Methods and devices for molding a desired configuration into an endovascular graft section that is made of a plurality of layers of fusible material. Layers of fusible material are disposed on a shape forming mandrel with seams in the layers that may be configured to produce inflatable channel. The graft section and shape forming mandrel can be placed in a mold which contains an outer layer or layers of fusible material while the inflatable channels are being expanded and the fusible material of the graft section fixed. In some embodiments, the fusible material of the graft section may be fixed by a sintering process.

26 Claims, 29 Drawing Sheets

U.S. PATENT DOCUMENTS

| | | | |
|---|---|---|---|
| 5,641,373 A | | 6/1997 | Shannon et al. |
| 5,653,745 A | * | 8/1997 | Trescony et al. .......... 623/1.29 |
| 5,667,523 A | | 9/1997 | Bynon et al. |
| 5,716,395 A | | 2/1998 | Myers et al. |
| 5,718,973 A | | 2/1998 | Lewis et al. |
| 5,789,047 A | | 8/1998 | Sasaki et al. |
| 5,871,538 A | | 2/1999 | Dereume |
| 5,931,865 A | | 8/1999 | Silverman et al. |
| 5,944,750 A | | 8/1999 | Tanner et al. |
| 5,961,545 A | | 10/1999 | Lentz et al. |
| 5,962,039 A | * | 10/1999 | Katou et al. ................ 425/210 |
| 5,993,489 A | | 11/1999 | Lewis et al. |
| 6,004,348 A | | 12/1999 | Banas et al. |
| 6,121,042 A | | 9/2000 | Peterson et al. |
| 6,143,022 A | | 11/2000 | Shull et al. |
| 6,149,681 A | | 11/2000 | Houser et al. |
| 6,187,054 B1 | | 2/2001 | Colone et al. |
| 6,214,039 B1 | | 4/2001 | Banas et al. |
| 6,245,099 B1 | | 6/2001 | Edwin et al. |
| 6,245,100 B1 | | 6/2001 | Davila et al. |
| 6,264,684 B1 | | 7/2001 | Banas et al. |
| 6,267,834 B1 | | 7/2001 | Shannon et al. |
| 6,280,467 B1 | | 8/2001 | Leonhardt |
| 6,296,661 B1 | | 10/2001 | Davila et al. |
| 6,306,164 B1 | | 10/2001 | Kujawski |
| 6,312,458 B1 | | 11/2001 | Golds |
| 6,312,462 B1 | | 11/2001 | McDermott et al. |
| 6,319,279 B1 | | 11/2001 | Shannon et al. |
| 6,344,055 B1 | | 2/2002 | Shukov |
| 6,357,104 B1 | | 3/2002 | Myers |
| 6,361,637 B2 | | 3/2002 | Martin et al. |
| 6,364,904 B1 | | 4/2002 | Smith |
| 6,368,347 B1 | | 4/2002 | Maini et al. |
| 6,398,803 B1 | | 6/2002 | Layne et al. |
| 6,402,779 B1 | | 6/2002 | Colone et al. |
| 6,425,855 B2 | | 7/2002 | Tomonto |
| 6,428,571 B1 | | 8/2002 | Lentz et al. |
| 6,443,981 B1 | | 9/2002 | Colone et al. |
| 6,451,047 B2 | | 9/2002 | McCrea et al. |
| 6,523,576 B2 | * | 2/2003 | Imaeda et al. ............... 138/121 |
| 6,540,780 B1 | | 4/2003 | Zilla et al. |
| 6,547,814 B2 | | 4/2003 | Edwin et al. |
| 6,547,815 B2 | | 4/2003 | Myers |
| 6,558,414 B2 | | 5/2003 | Layne |
| 2001/0023370 A1 | | 9/2001 | Smith et al. |
| 2001/0036522 A1 | | 11/2001 | Hanada et al. |
| 2001/0039446 A1 | | 11/2001 | Edwin et al. |
| 2001/0049550 A1 | | 12/2001 | Martin et al. |
| 2001/0053929 A1 | | 12/2001 | Vonesh et al. |
| 2002/0002397 A1 | | 1/2002 | Martin et al. |
| 2002/0026231 A1 | | 2/2002 | Shannon et al. |
| 2002/0032408 A1 | | 3/2002 | Parker et al. |
| 2002/0040236 A1 | | 4/2002 | Lau et al. |
| 2002/0040237 A1 | | 4/2002 | Lentz et al. |
| 2002/0045931 A1 | | 4/2002 | Sogard et al. |
| 2002/0055768 A1 | | 5/2002 | Hess et al. |
| 2002/0099435 A1 | | 7/2002 | Stinson |
| 2002/0111667 A1 | | 8/2002 | Girton et al. |
| 2002/0138129 A1 | | 9/2002 | Armstrong et al. |
| 2002/0156521 A1 | | 10/2002 | Ryan et al. |
| 2002/0173836 A1 | | 11/2002 | Pinchuk |
| 2003/0006528 A1 | | 1/2003 | Edwin et al. |
| 2003/0009211 A1 | | 1/2003 | DiCarlo |
| 2003/0097174 A1 | | 5/2003 | Henderson |

* cited by examiner

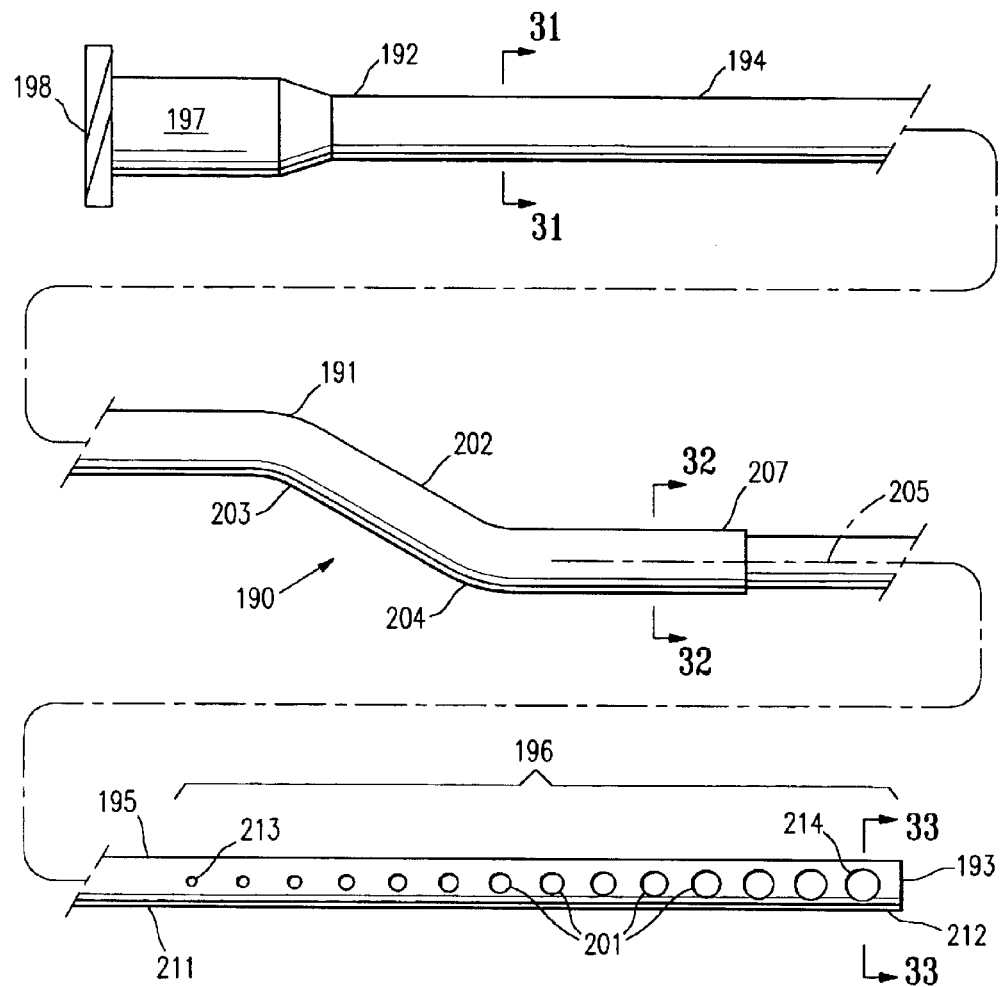
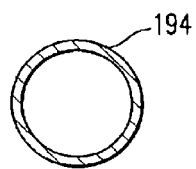 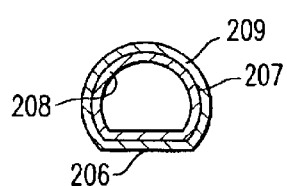 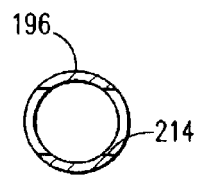
FIG. 30
FIG. 31   FIG. 32   FIG. 33

METHOD AND APPARATUS FOR SHAPE FORMING ENDOVASCULAR GRAFT MATERIAL

RELATED APPLICATIONS

This application is related to U.S. patent application Ser. No. 10/029,584, filed Dec. 20, 2001 entitled "Endovascular Graft Joint and Method for Manufacture", by Chobotov et al., U.S. patent application Ser. No. 10/029,559, filed Dec. 20, 2001, entitled "Advanced Endovascular Graft", by Chobotov et al., and U.S. patent application Ser. No. 10/029,557, filed Dec. 20, 2001, entitled "Method and Apparatus for Manufacturing an Endovascular Graft Section", by Chobotov et al. All of the above applications are commonly owned and were on even date herewith. All of the above applications are hereby incorporated by reference, each in their entirety.

BACKGROUND

Embodiments of the device and method discussed herein relate to a system and method for manufacturing intracorporeal devices used to replace, strengthen, or bypass body channels or lumens of patients; in particular, those channels or lumens that have been affected by conditions such as abdominal aortic aneurysms.

Existing methods of treating abdominal aortic aneurysms include invasive surgical methods with grafts used to replace the diseased portion of the artery. Although improvements in surgical and anesthetic techniques have reduced perioperative and postoperative morbidity and mortality, significant risks associated with surgical repair (including myocardial infarction and other complications related to coronary artery disease) still remain.

Due to the inherent hazards and complexities of such surgical procedures, various attempts have been made to develop alternative repair methods that involve the endovascular deployment of grafts within aortic aneurysms. One such method is the non-invasive technique of percutaneous delivery of grafts and stent-grafts by a catheter-based system. Such a method is described by Lawrence, Jr. et al. in "Percutaneous Endovascular Graft: Experimental Evaluation", *Radiology* (1987). Lawrence et al. describe therein the use of a Gianturco stent as disclosed in U.S. Pat. No. 4,580,568 to Gianturco. The stent is used to position a Dacrone® fabric graft within the vessel. The Dacrono® graft is compressed within the catheter and then deployed within the vessel to be treated.

A similar procedure is described by Mirich et al. in "Percutaneously Placed Endovascular Grafts for Aortic Aneurysms: Feasibility Study," *Radiology* (1989). Mirich et al. describe therein a self-expanding metallic structure covered by a nylon fabric, the structure being anchored by barbs at the proximal and distal ends.

An improvement to percutaneously delivered grafts and stent-grafts results from the use of materials such as expanded polytetrafluoroethylene (ePTFE) for a graft body. This material, and others like it, have clinically beneficial properties. However, manufacturing a graft from ePTFE can be difficult and expensive. For example, it is difficult to bond ePTFE with conventional methods such as adhesives, etc. In addition, depending on the type of ePTFE, the material can exhibit anisotropic behavior. Grafts are generally deployed in arterial systems whose environments are dynamic and which subject the devices to significant flexing and changing fluid pressure flow. Stresses are generated that are cyclic and potentially destructive to interface points of grafts, particularly interface between soft and relatively hard or high strength materials.

What has been needed is a method and device for manufacturing intracorporeal devices used to replace, strengthen or bypass body channels or lumens of a patient from ePTFE and similar materials which is reliable, efficient and cost effective.

SUMMARY

An embodiment of the invention is directed to a mold for manufacture of an endovascular graft, or section thereof, which has at least one inflatable channel or cuff. The mold has a plurality of mold body portions configured to mate with at least one other mold body portion to produce an assembled mold having a main cavity portion. The main cavity portion has an inside surface contour that matches an outside surface contour of the graft section with the at least one inflatable channel or cuff in an expanded state. In some embodiments, the main cavity portion may include channel cavities, cuff cavities, longitudinal channel cavities or helical channel cavities which are configured to correspond to inflatable channels, inflatable cuffs, inflatable longitudinal channels or inflatable helical channels of the graft when in an expanded state. In other embodiments, the mold can have a plurality of circumferential channel cavities and at least one longitudinal channel cavity or helical channel cavity that transects the circumferential channel cavities.

Another embodiment is directed to an outer constraint device in the form of a mold for manufacture of an endovascular graft, or section thereof, which has at least one inflatable channel or cuff. The mold has a first mold body portion having a main cavity portion with an inside surface contour that is live configured to correspond to an outside surface contour of the graft section with the at least one inflatable channel or cuff In an expanded state. The mold also has a second mold body portion configured to mate with the first mold body portion having a main cavity portion with an inside surface contour that is configured to correspond to an outside surface contour of the graft section with the at least one inflatable channel or cuff in an expanded state.

A further embodiment of the invention is directed to a pressure line for use in the manu facture of an endovascular graft, or section thereof. The pressure line has an elongate conduit with an input end, an output end and a permeable section. The permeable section can have a permeability gradient which increases with distance from the input end. In one embodiment, the permeability of the pressure line increases about 5 to about 20 percent per centimeter in a direction from the input end to the output end along the permeable section. The permeability gradient in the permeable section can be created by a plurality of outlet orifices in the elongate conduit which increase in diameter with an increase in distance from input end. In addition, such outlet orifices can be spaced longitudinally from each other so as to match a longitudinal spacing of a plurality of circumferential inflatable channels of the endovascular graft.

Another embodiment of the invention includes a mandrel for shape forming an endovascular graft, or section thereof. The mandrel has a middle section and a first end section with at least a portion which has a larger outer transverse dimension than an outer transverse dimension of the middle section and which is removably secured to a first end of the middle section. A second end section is disposed at a second end of the middle section with at least a portion which has a larger outer transverse dimension than an outer transverse dimension of the middle section. In a particular embodiment, the first end section and second end section are removably secured to the middle section by threaded portions and a longitudinal axis of the first end section, second end section and middle section can be substantially coaxial. In another embodiment, the middle section can have a pressure line recess in the form of a longitudinal channel in an outer surface of the middle section which is configured to accept a pressure line.

Embodiments of the invention can include an assembly for manufacture of an endovascular graft, or section thereof, which has at least one inflatable cuff or channel on a section thereof. The assembly consists of a mandrel having an elongate body having an outer surface counter configured to support an inside surface of the graft section. The graft section having at least one inflatable cuff or channel is disposed about at least a portion of the mandrel. A pressure line having an elongate conduit with an input end, an output end and a permeability gradient which increases with distance from the input end is in fluid communication with an inflatable cuff or channel of the graft section. A mold is at least partially disposed about the graft section, the pressure line and the mandrel. The mold has a plurality of mold body portions configured to mate together to produce an assembled mold having a main cavity portion. The main cavity portion has an inside surface contour that matches an outside surface contour of the graft section with the at least one inflatable cuff or channel in an expanded state. The inside surface contour is configured to radially constrain an outer layer or layers of the at least one inflatable cuff or channel during expansion of the cuff or channel. In some embodiments, the plurality of orifices of the elongate conduit of the pressure line can be substantially aligned with circumferential channel cavities of the mold.

Embodiments of the invention which include methods for forming an inflatable channel or cuff of an endovascular graft, or section thereof, will now be described. An graft section is provided with at least one inflatable channel or cuff formed between layers of graft material of the graft section in an unexpanded state. A mold is provided which has a main cavity portion with an inside surface contour that corresponds to an outside surface contour of the graft section with the at least one inflatable channel or cuff in an expanded state. The graft section is then positioned in the main cavity portion of the mold with the at least one inflatable channel or cuff of the graft section in an unexpanded state positioned to expand into corresponding channel or cuff cavity portions of the main cavity portion. Once the graft section is properly positioned within the main cavity portion of the mold, pressurized gas is injected into the at least one inflatable channel or cuff to expand the at least one inflatable channel or cuff. Thereafter, the graft material of the at least one inflatable channel or cuff is fixed with the at least one inflatable channel or cuff in an expanded state.

In a particular embodiment of the method, a pressure line having an elongate conduit with a permeable section which includes a permeability gradient can be placed in fluid communication with at least one inflatable channel or cuff of the graft section. Thereafter, pressurized gas can be injected into the at least one inflatable channel or cuff through the permeable section of the pressure line. In addition, an optional internal radial support can be positioned within the graft section prior to expansion of the at least one inflatable channel or cuff. The internal radial support may consist of a mandrel which is disposed within the graft section prior to placing the graft section into the mold so as to radially support the inside surface of the graft section during injection of the pressurized gas. In one embodiment, the graft material of the at least one inflatable channel or cuff is fixed by sintering. In another embodiment of a method for forming at least one inflatable channel or cuff of an endovascular graft, or section thereof, a pressurized liquid can be injected into the inflatable channel or cuff of the graft section. Some expansion of the inflatable channel or cuff can be carried out by vapor pressure from boiling of pressurized liquid during fixing of the graft material with the liquid in the inflatable channel or cuff.

BRIEF DESCRIPTION OF THE DRAWINGS

FIG. 30 shows an elevational view of a pressure line having features of the invention.

FIG. 31 is a transverse cross sectional view of the pressure line of FIG. 30 taken at lines 31—31.

FIG. 32 is a transverse cross sectional view of the pressure line of FIG. 30 taken at lines 32—32, which shows a D-shaped configuration of a portion of the pressure line.

FIG. 33 is a transverse cross sectional view of the pressure line with exit ports of FIG. 30 taken at lines 33—33.

DETAILED DESCRIPTION

Figure 1:
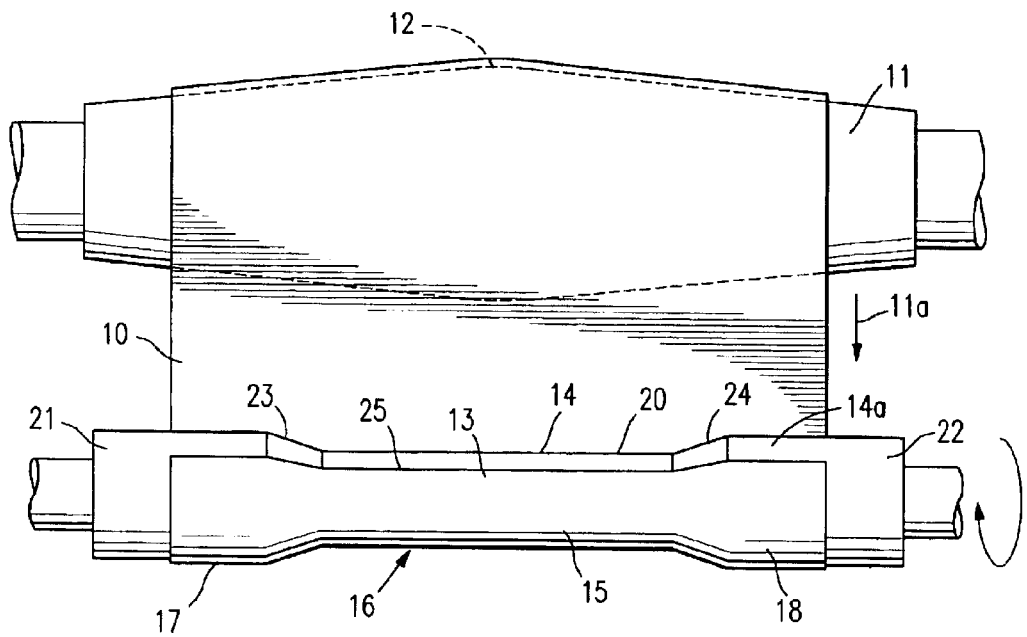
FIG. 1 illustrates a layer of fusible material being positioned onto a shape forming mandrel.

FIG. 1 illustrates a sheet of fusible material 10 stored on an elongate drum 11. The drum 11 is rotatable, substantially circular in transverse cross section and has a transverse dimension in the longitudinal center 12 that is greater than the transverse dimension of either end of the drum. The sheet of fusible material 10 is being rolled from the elongate drum in a single layer 13 onto an interior surface support means in the form of a cylindrical or tapered (conical) shape forming member or mandrel 14 to form a body section 15 of an endovascular graft 16. The body section 15 has a proximal end 17 and a distal end 18. For the purposes of this application, with reference to endovascular graft devices, the proximal end 17 describes the end of the graft that will be oriented towards the oncoming flow of bodily fluid, usually blood, when the device is deployed within a conduit of a patient's body. The distal end 18 of the graft is the end opposite the proximal end.

A single layer of fusible material 13 is a term that generally refers to a sheet of material that is not easily separated by mechanical manipulation into additional layers. The shape forming mandrel 14 is substantially cylindrical in configuration, although other configurations are possible. Middle section 20 of mandrel 14 shown in FIGS. 1–2 has a transverse dimension which is smaller than the transverse dimension of a first end section 21 and a second end section 22. The shape forming mandrel may have a first tapered section 23 at the first end and a second tapered section 24 at the second end. The sheet of fusible material 10 is shown being rolled off the elongate drum 11 in the direction indicated by the arrow 11A with the lead end 25 of the first layer of fusible material 10 oriented longitudinally along an outside surface 14A of the shape forming mandrel 14.

The fusible material in the embodiment illustrated in FIG. 1 is ePTFE that ranges from about 0.0005 to about 0.010 inch in thickness; specifically from about 0.001 to about 0.003 inch in thickness. The sheet being disposed or rolled onto the shape forming mandrel 14 may range from about 2 to about 10 inches in width; specifically, from about 3 to about 7 inches in width, depending on the indication and size of the end product.

The ePTFE material sheet 10 in FIG. 1 is a fluoropolymer with a node and fibril composition with the fibrils oriented in primarily a uniaxial direction substantially aligned with the longitudinal axis of shape forming mandrel 14. Other nodal/fibril orientations of ePTFE could also be used for this layer, including multiaxially oriented fibril configurations or uniaxial material oriented substantially circumferentially about shape forming mandrel 14 or at any desired angle between substantial alignment with the longitudinal axis and substantial alignment with a circumferential line about the shape forming mandrel 14. Uniaxially oriented ePTFE materials tend to have greater tensile strength along the direction of fibril orientation, so fibril orientation can be chosen to accommodate the greatest stresses imposed upon the finished product for the particular layer, combination of layers, and portion of the product where such stress accommodation is needed.

The layers of fusible material made of ePTFE are generally applied or wrapped in an unsintered state. By applying the ePTFE layers in an unsintered or partially sintered state, the graft body section 15, upon tat completion, can then be sintered or fixed as a whole in order to form a cohesive monolithic structure with all contacting surfaces of ePTFE layers achieving some level of interlayer adhesion. It may, however, be desirable to apply some layers of fusible material that have been pre-sintered or pre-fixed in order to achieve a desired result or to assist in the handling of the materials during the construction process. For example, it may be desirable in some embodiments to sinter the single layer 13 of fusible material applied to the shape forming mandrel 14 in order to act as a better insulator between the shape forming mandrel 14, which can act as a significant heat sink, and subsequent layers of fusible material which may be welded by seam formation in some locations in order to create inflatable channels.

The amount of expansion of the ePTFE material used for the construction of endovascular grafts and other devices can vary significantly depending on the desired characteristics of the material and the finished product. Typically, the ePTFE materials processed by the devices and methods discussed herein may have a density ranging from about 0.4 to about 2 grams/cc; specifically, from about 0.5 to about 0.9 grams/cc. The nodal spacing of the uniaxial ePTFE material may range from about 0.5 to about 200 microns; specifically, from about 5 to about 35 microns. The nodal spacing for multiaxial ePTFE material may range from about 0.5 to about 20 microns; specifically, from about 1 to about 2 microns.

Although FIG. 1 illustrates a layer of fusible material that is made of ePTFE, the methods described herein are also suitable for a variety of other fusible materials. Examples of other suitable fusible materials for endovascular graft construction and other applications include PTFE, porous PTFE, ultra high molecular weight polyethylene, polyesters, and the like.

Figure 2:
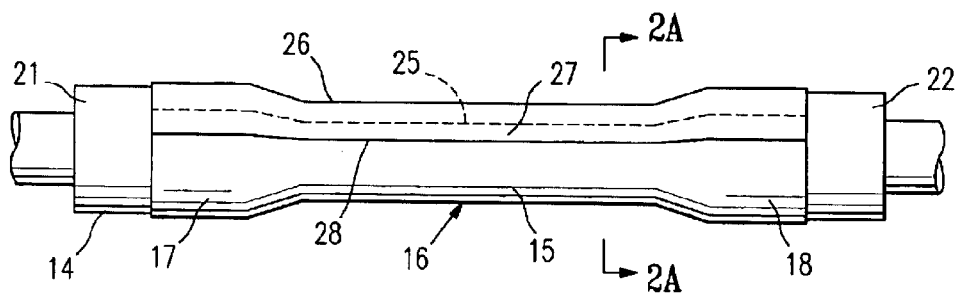
FIG. 2 shows a first layer of fusible material disposed on a shape forming mandrel.
Figure 2A:
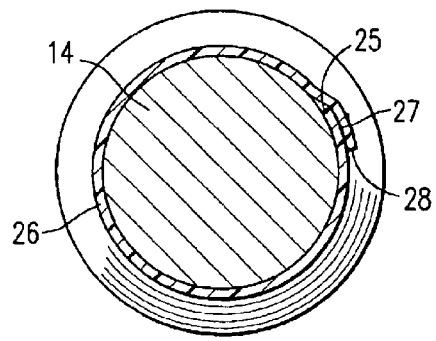
FIG. 2A is a transverse cross sectional view of the first layer of fusible material and the shape forming mandrel of FIG. 2 taken along lines 2A—2A in FIG. 2.

FIGS. 2 and 2A depict a first layer of fusible material 26 disposed on the shape forming mandrel 14 with an overlapped portion 27 of the first layer 26 on itself. A terminal end 28 of the first layer 26 is seen extending longitudinally along the length of the shape forming mandrel 14. As the layer of fusible material is wrapped onto shape forming mandrel 14, some tension may be provided on the sheet of material by the elongate drum 11. As a result of this tension and the flexible and conforming properties of the ePTFE material, the first layer of material 26 conforms closely to the outer contour of the shape forming mandrel 14 as is illustrated in FIG. 2.

In some embodiments, it may be desirable to pass the tip of a seam forming tool or similar device (not shown) along the overlapped portion 27 of first layer 26 in a longitudinal direction in order to form a seam (not shown) along the overlapped portion 27 of first layer 26. A tool suitable for forming such a longitudinal seam is a soldering iron with a smooth, rounded tip that will not catch or tear the layer of fusible material. An appropriate operating temperature for the tip of such a tool may range from about 320 to about 550 degrees Celsius; specifically, from about 380 to about 420 degrees Celsius.

Figure 3:
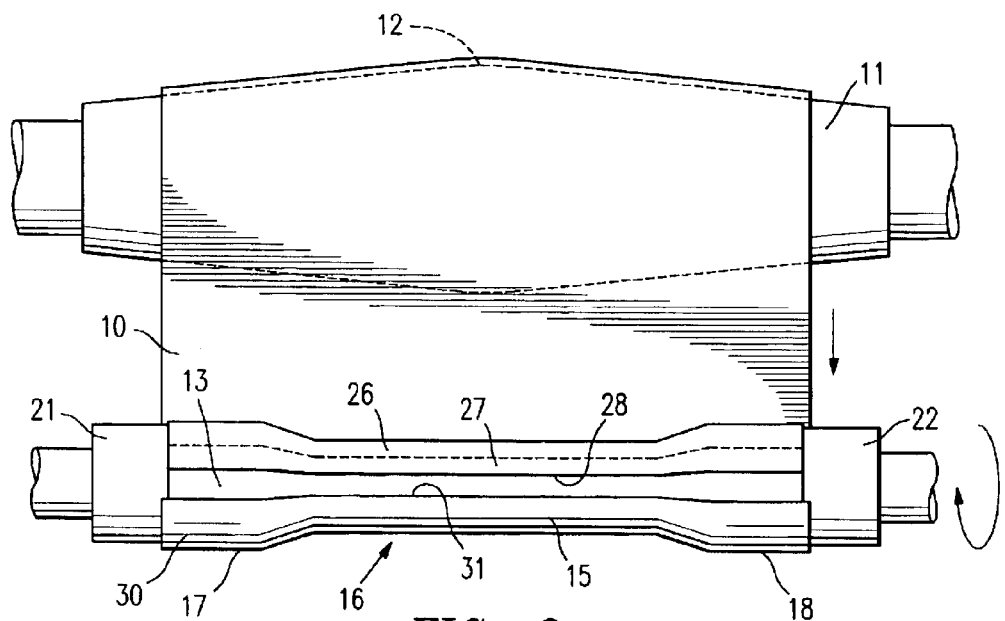
FIG. 3 illustrates an additional layer of fusible material being deposited onto a shape forming mandrel.

FIG. 3 illustrates an additional layer of fusible material 30 being disposed or wrapped onto the first layer of fusible material 26 in a manner similar to that described above for the first layer 26. Both uniaxial and multiaxial ePTFE may be used for this additional layer 30. A lead end 31 of the additional layer can be seen adjacent the terminal end 28 of the first layer 26. Tension on the additional layer of fusible material 30 helps to make the additional layer 30 conform to the shape forming mandrel 14 as seen in the illustration. Although a single additional layer 30 is shown in FIG. 3 as being disposed onto the first layer 26, it is within the scope of the invention to wrap multiple additional layers 30 of fusible material in this step. We have found that wrapping two additional layers 30 of multiaxial ePTFE onto the first layer 26 helps to form a useful graft body section 15.

Figure 4:
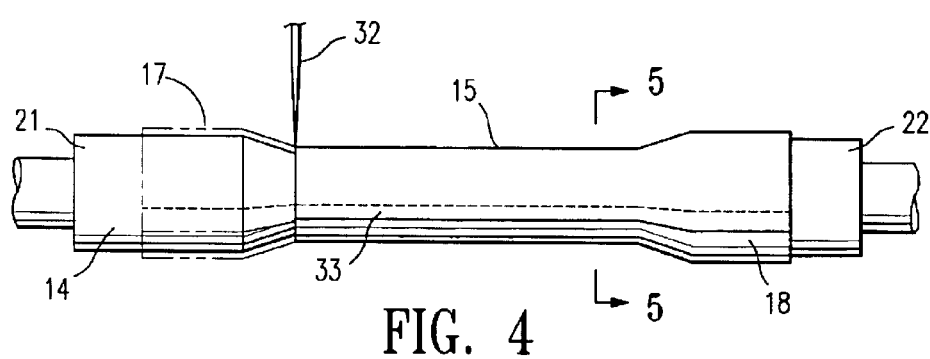
FIG. 4 shows the first layer of fusible material being trimmed by an instrument.
Figure 5:
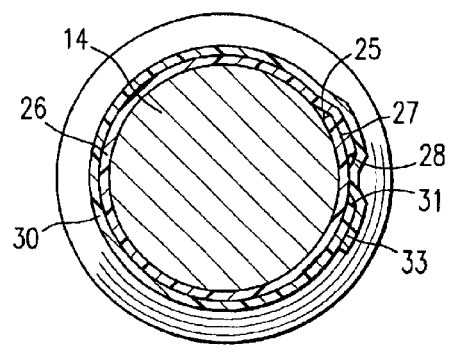
FIG. 5 is a transverse cross sectional view of the layers of fusible material and shape forming mandrel of FIG. 5 taken along lines 5—5 of FIG. 4.

FIG. 4 shows an optional step in which the first and additional layers of fusible material 26 and 30 which form the graft body section 15 under construction are trimmed by knife edge 32 or a similar tool which is pressed against the layers of material and moved circumferentially about the shape forming mandrel 14. FIG. 5 is a transverse cross sectional view of the shape forming mandrel 14 and graft body section 15 of FIG. 5 taken along lines 5—5 in FIG. 4. The overlapped portion 27 of the first layer 26 and an overlapped portion 33 of the additional layer 30 of fusible material can be seen. It may be desirable to create a longitudinal seam in the overlapped portion 33 of the additional layer 30 in a manner similar to that of the first layer 26 discussed above using the same or similar tools.

Figure 6:
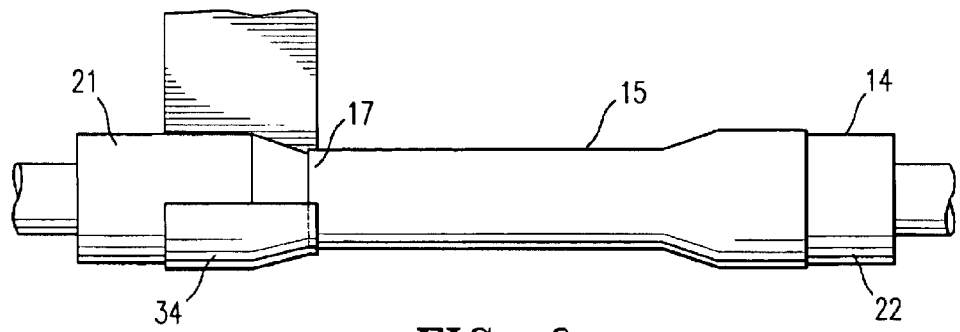
FIG. 6 illustrates additional layers of fusible material being deposited on the shape forming mandrel.

FIG. 6 illustrates a proximal end wrap 34 of fusible material being applied to the additional layer 30 of graft body section 15, preferably under some tension. We have found it useful to have end wrap 34 be uniaxial ePTFE, with the fibrils of the end wrap material oriented circumferentially about the shape forming mandrel 14, although other orientations and types of ePTFE are possible. The end wrap material may have a thickness ranging from about 0.0005 to about 0.005 inch; specifically, from about 0.001 to about 0.002 inch. The width of the end wrap material may range from about 0.25 to about 2.0 inch; specifically, from about 0.5 to about 1.0 inch. One or more layers of end wrap 34 (in any desired orientation) may be built up onto the proximal end 17 of graft body section 15 on shape forming mandrel 14. The additional end wrap layer or layers 34 may be applied in a manner similar to that of the first layer 26 and additional layers 30 as discussed above.

Figure 7:
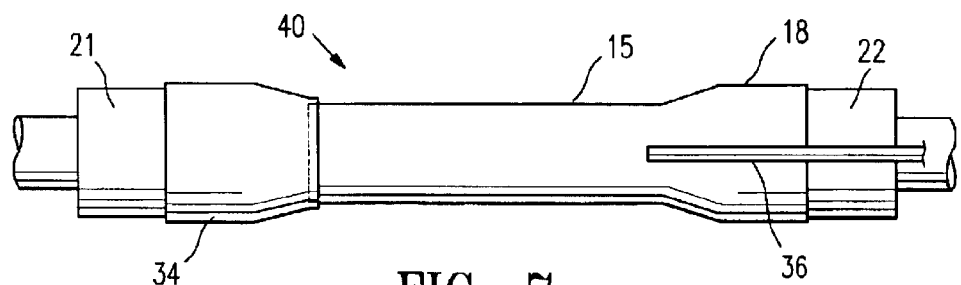
FIG. 7 illustrates an inflation line being positioned on the first and additional layers of fusible material of FIG. 6.
Figure 7A:
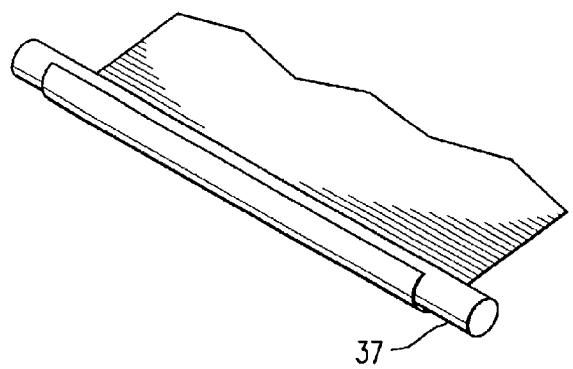
FIGS. 7A and 7B illustrate the formation of the inflation line of FIG. 7.
Figure 7B:
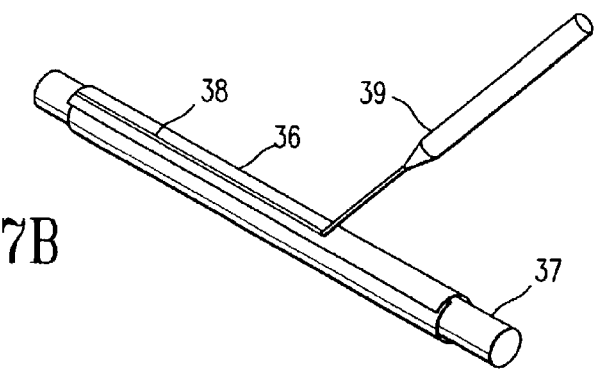

FIG. 7 shows graft body section 15 with the end wrap layer 34 completed with an inflation line 36 disposed on or near the distal end 18 of graft body section 15. The inflation line 36 may be constructed as shown in FIGS. 7A and 7B of ePTFE by wrapping one or more layers of the material about a cylindrical mandrel 37. A longitudinal seam 38 can then be formed in an overlapped portion of the layers by passing the tip of a seam forming tool 39 along the overlapped portion of the first layer in a longitudinal direction in order to form a seam 38 along the overlapped portion of the layers of the inflation line 36. A tool suitable for forming such a longitudinal seam is a soldering iron with a smooth rounded tip that will not catch or tear the layer of fusible material; operating temperatures for the tip may range as previously discussed. Alternatively, the inflation line 36 may be formed using an ePTFE extrusion placed over a mandrel.

Once seam 38 is formed in inflation line 36, the fusible material of inflation line 36 may can be fixed or sintered by heating to a predetermined temperature for a predetermined time. For embodiments of the inflation line 36 made of ePTFE, the layers are sintered by bringing the layered assembly to a temperature ranging from about 335 to about 380 degrees Celsius (for unsintered material) and about 320 to about 380 degrees Celsius (for sintering material that was previously sintered) and then cooling the assembly to a temperature ranging from about 180 to about 220 degrees Celsius. The inflation line 36 may then be removed from mandrel 37 and disposed on a graft body assembly 40 as shown in FIG. 7. The inflation line 36 may be pre-fixed or pre-sintered to avoid having the inner surfaces of the inflation line 36 stick together during the construction and processing of the graft and possibly block the inflation line 36.

Figure 8:
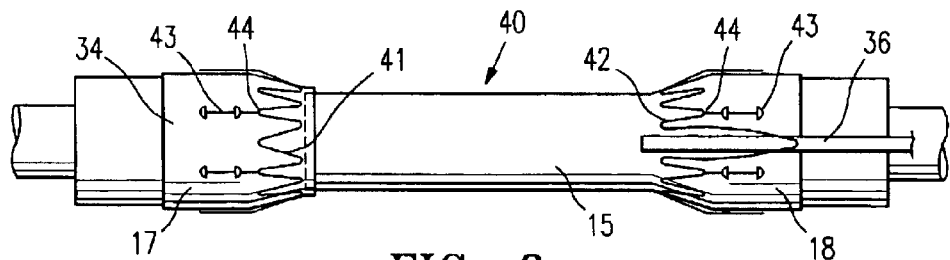
FIG. 8 shows two expandable members positioned on the layers of fusible material of FIG. 7.

In FIG. 8, expandable members in the form of a proximal connector member 41 and a distal connector member 42 have been disposed onto the graft body section 15 towards the respective graft body section proximal end 17 and distal end 18. The proximal connector member 41 is an elongate flexible metal element configured as a ring, with the ring having a zig-zag or serpentine pattern around the circumference of the ring. The distal connector member 42 can have a similar configuration; note the feature of this element in which an extended apex 44 is disposed over inflation line 36 to further stabilize graft section 15. This configuration allows the connector members 41 and 42 to be radially constrained and radially expanded while maintaining a circular ring configuration. The embodiment of the connector members 41 and 42 shown in FIG. 8 may be constructed of any suitable biocompatible material; most suitable are metals, alloys, polymers and their composites known to have superelastic properties that allow for high levels of strain without plastic deformation, such as nickel titanium (NiTi). Other alloys such as stainless steel may also be used. Connector members 41 and 42 shown are also configured to be self-expanding from a radially constrained state. The serpentine pattern of the connector members 41 and 42 is disposed over base layers of the graft body section as are connector elements 43 which are disposed on certain apices 44 of the serpentine pattern of the connector members 41 and 42. The embodiments of the connector members 41 and 42 shown in FIG. 8 have been shape formed to lie substantially flat against the contour of the outer surface of the shape forming mandrel 14. Although the embodiment of FIG. 8 illustrates connector members 41 and 42 being disposed upon the graft body section 15, expandable members including stents or the like may be used in place of the connector members 41 and 42.

Figure 9:
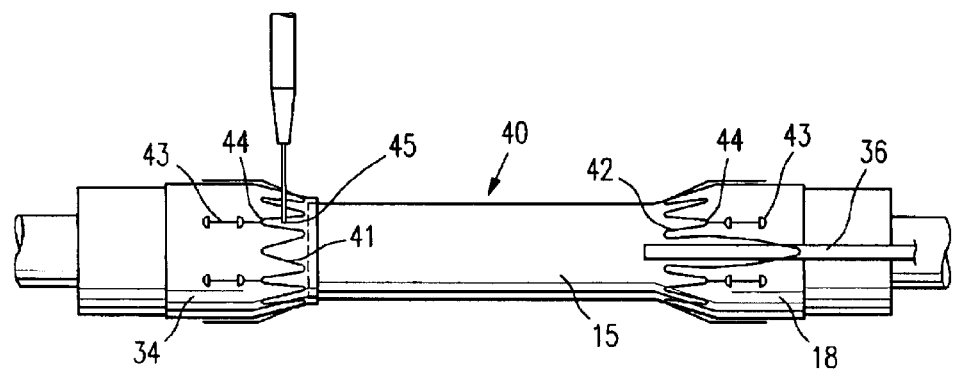
FIG. 9 illustrates the deposition of an adhesive or melt processible material adjacent a connector member of the graft body section under construction.

An optional adhesive or melt-processible material such as FEP or PFA may be deposited adjacent the connector members 41 and 42 prior to the addition of additional layers of fusible material to the graft body section 15, as is shown in FIG. 9. Materials such as FEP or PFA can help the layers of fusible material to adhere to the connector members 41 and 42, to inflation line 36 (in the case of distal member 42), and to each other. In addition, such material may serve to provide strain relief between connector members 41 and 42 and the adhered or bonded layers of fusible material (and inflation line 36) adjacent the wire of the connector members 41 and 42. It has been determined that one of the areas of greatest concentrated stress within an endovascular structure such as that described herein, when deployed within a dynamic biological system, such as an artery of a human patient, is at the junction between the connector members 41 and 42 and graft body section 15. Therefore, it may be desirable to include materials such as FEP or PFA or some other form of strength enhancement or strain relief in the vicinity of this junction.

Figure 10:
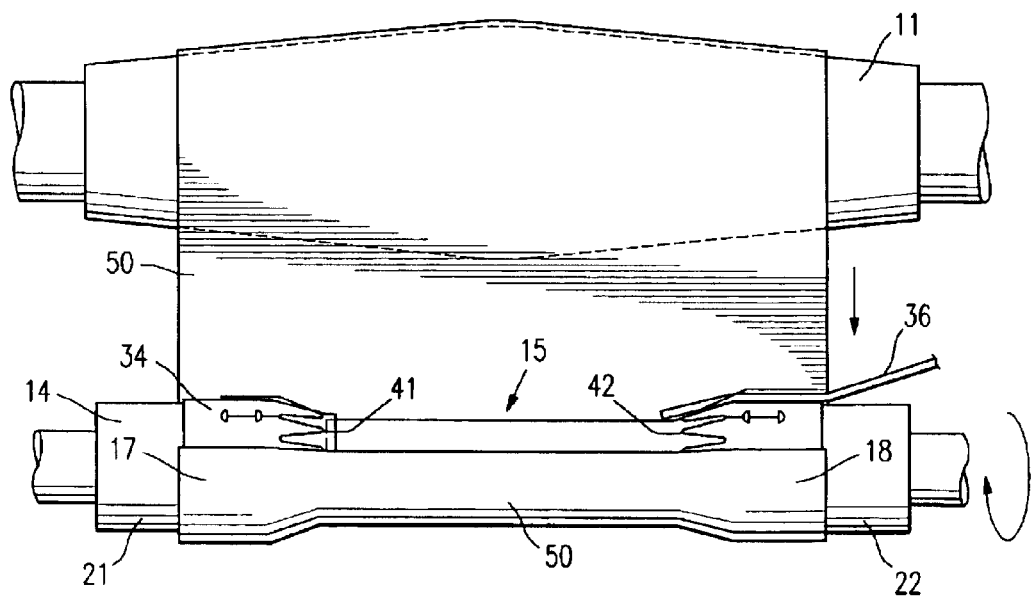
FIG. 10 shows another additional layer of fusible material being deposited onto the graft body section.

An outer overall wrap layer 50 may thereafter be applied to the graft body section 15 and connector members 41 and 42 as shown in FIG. 10. The outer overall wrap layer 50 can include one, two, three or more layers of multiaxial ePTFE, usually about 2 to about 4 layers, but uniaxial ePTFE other suitable fusible materials, fibril orientation and layer numbers could also be used. The outer overall wrap layer 50 is most usefully applied under some tension in order for the layer or layers to best conform to the outer contour of the shape forming mandrel 14 and graft body section 15. When the outer layer 50 comprises multiaxial ePTFE, there is generally no substantially preferred orientation of nodes and fibrils within the microstructure of the material. This result in a generally isotropic material whose mechanical properties, such as tensile strength, are generally comparable in all directions (as opposed to significantly different properties in different directions for uniaxially expanded ePTFE). The density and thickness of the multiaxial material can be the same as or similar to those dimensions discussed above.

Although not shown in the figures, we have found it useful to add one or more optional cuff-reinforcing layers prior to the addition of an overall wrap layer 50 as discussed below in conjunction with FIG. 10. Typically this cuff-reinforcing layer is circumferentially applied to graft body section 15 at or near the graft body section proximal end 17 so to provide additional strength to the graft body section proximal end 17 in those designs in which a proximal cuff (and possibly a proximal rib) are used. Typically the graft experiences larger strains during fabrication and in service in the region of the proximal cuff, especially if a larger cuff is present. This optional cuff-reinforcing layer typically is multiaxial ePTFE, although uniaxial ePTFE and other materials may be used as well. We have found effective a cuff-reinforcing layer width from about 20 to about 100 mm; specifically, about 70 mm. Functionally, however, any width sufficient to reinforce the proximal end of graft body section 15 may be used.

Figure 11:
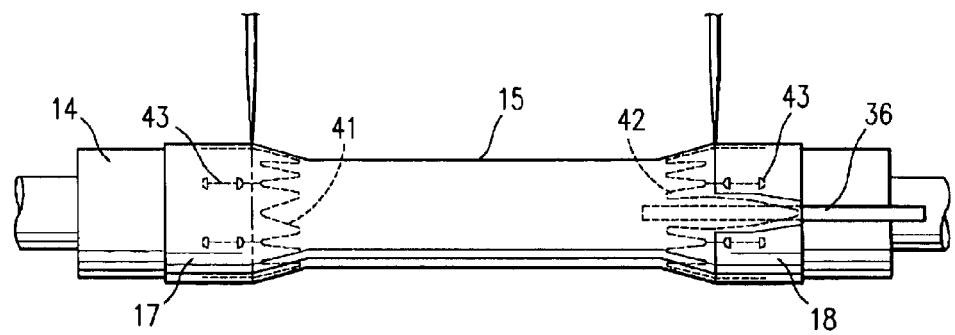
FIG. 11 illustrates excess fusible material being trimmed from the first end and second end of the graft body section adjacent the connector a members.
Figure 12:
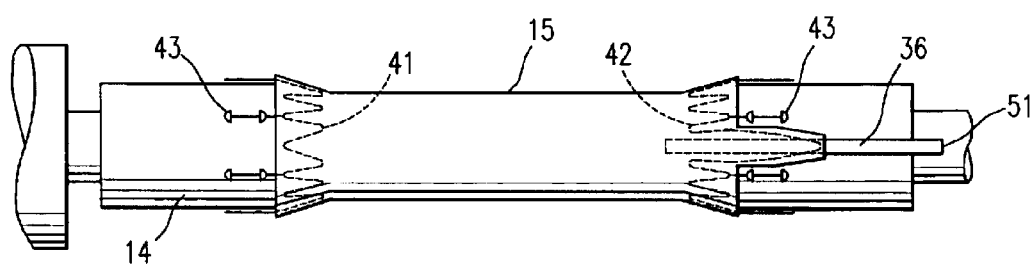
FIG. 12 is an elevational view of the graft body section with the fusible material trimmed away and removed.

Once the additional layer or layers of fusible material and additional graft elements such as the connector members 41 and 42 and inflation line 36 have been applied, any excess fusible material may be trimmed away from the proximal end 17 and distal end 18 of graft body section 15. FIG. 11 illustrates one or more layers of fusible material being trimmed from the proximal end 17 and distal end 18 of the graft body section 15 so as to leave the connector members 41 and 42 embedded between layers of fusible material but with the connector elements 43 exposed and a distal end 51 of the inflation line 36 exposed as shown in FIG. 12. Once the fusible material has been trimmed from the proximal end 17 and the distal end 18, as discussed above, an additional process may optionally be performed on the proximal end 17, distal end 18 or both the proximal end and distal end 17 and 18. In this optional process (not shown in the figures), the outer wrap 50 is removed from a portion of the connector members 41 and 42 so as to expose a portion of the connector members 41 and 42 and the additional layer of fusible material 30 beneath the connector member 42 and the proximal end wrap 34 beneath connector member 41. Once exposed, one or more layers of the additional layer or layers 30 or proximal end wrap 34 may have cuts made therein to form flaps which can be folded back over the respective connector members 42 and 41 and secured to form a joint (not shown). One or more layers of fusible material can then be disposed over such a joint to provide additional strength and cover up the joint. The construction of such a joint is discussed in copending U.S. Patent Application "Endovascular Graft Joint and Method for Manufacture" by Chobotov et al. which has been incorporated by reference herein.

Once the graft body section 15 has been trimmed, the entire shape forming mandrel 14 and graft body section 15 assembly is moved to a seam forming apparatus 52 illustrated in FIGS. 13A–13H. This seam forming apparatus 52 has a base 53 and a vertical support platform 54 which extends vertically upward from the back edge of the base 53. A mount system 55 is secured to the base 53 and for the embodiment shown in the figures, consists of a motor drive chuck unit 56 secured to a riser 57 and a live center unit 58 secured to a riser 59. Both risers 57 and 59 are secured to the base 53 as shown. The axis of rotation 55A of the chuck 60 of the motor drive chuck unit 56 and the axis of rotation 55B of the live center 61 of the live center unit 58 are aligned or concentric as indicated by dashed line 55C. A motor is mechanically coupled to the chuck 60 of the motor drive chuck unit 56 and serves to rotate the chuck 60 in a controllable manner.

A vertical translation rack 62 is secured to the vertical support platform 54 and extends from the base 53 to the top of the vertical support platform 54. A vertical car 63 is slidingly engaged on the vertical translation rack 62 and can be moved along the vertical translation rack 62, as shown by arrows 63A, in a controllable manner by a motor and pinion assembly (not shown) secured to the vertical car 63. A horizontal translation rack 64 is secured to the vertical car 63 and extends from the left side of the vertical car 63 to the right side of the vertical car 63. A horizontal car 65 is slidingly engaged on the horizontal translation rack 64 and can be moved along the horizontal rack 64, as shown by arrow 64A, in a controllable manner by a motor and pinion assembly (not shown) which is secured to the horizontal car 65.

A stylus rotation unit 66 is slidingly engaged with a second horizontal translation rack 65A disposed on the horizontal car 65 and can be moved towards and away from the vertical car 63 and vertical support platform 54 in a controllable manner as shown by arrow 66A. A stylus rotation shaft 67 to extends vertically downward from the stylus rotation unit 66 and rotates about an axis as indicated by dashed line 67B and arrow 67A in a controllable manner. A stylus mount 68 is secured to the bottom end of the rotation shaft 67 and has a main body portion 69 and a stylus pivot shaft 70. A stylus housing 71 is rotatably secured to the stylus mount 68 by the stylus pivot shaft 70. A torsion spring 72 is disposed between the proximal end of the stylus housing 73 and the stylus mount 68 and applies a predetermined amount of compressive, or spring-loaded force to the proximal end 73 of the stylus housing 71. This in turn determines the amount of tip pressure applied by a distal extremity 80 of a stylus tip 75 disposed at the distal end section 78 of the stylus 79 (which is in turn secured to the distal end section 76 of the stylus housing 71).

The base 53 of seam forming apparatus 52 is secured to a control unit housing 77 which contains one or more power supplies, a CPU, and a memory storage unit that are used in an automated fashion to control movement between the graft body 15 section and the stylus tip 75 in the various degrees of freedom therebetween. The embodiment of the seam forming apparatus 52 described above has five axes of movement (or degrees of freedom) between an object secured to the chuck 60 and live center 61 and the stylus tip 75; however, it is possible to have additional axes of movement, such as six, seven, or more. Also, for some configurations and seam forming processes, it may be possible to use fewer axes of movement, such as two, three, or four. In addition, any number of configurations may be used to achieve the desired number of degrees of freedom between the stylus 79 and the mounted device. For example, additional axes of translation or rotation could be added to the mount system and taken away from the stylus rotation unit 66. Although the embodiment of the shape forming mandrel 14 shown in FIGS. 1–17 is cylindrical, a five axis or six axis seam forming apparatus has the capability and versatility to accurately create seams of most any desired configuration on a shape forming member or mandrel of a wide variety of shapes and sizes. For example, a "Y" shaped mandrel suitable for generating a bifurcated graft body section could be navigated by the five axis seam forming apparatus illustrated herein, as well as other shapes. Finally, seam forming apparatus 52 illustrated herein is but one of a number of devices and configurations capable of achieving the seams of the present inventions.

Figure 13A:
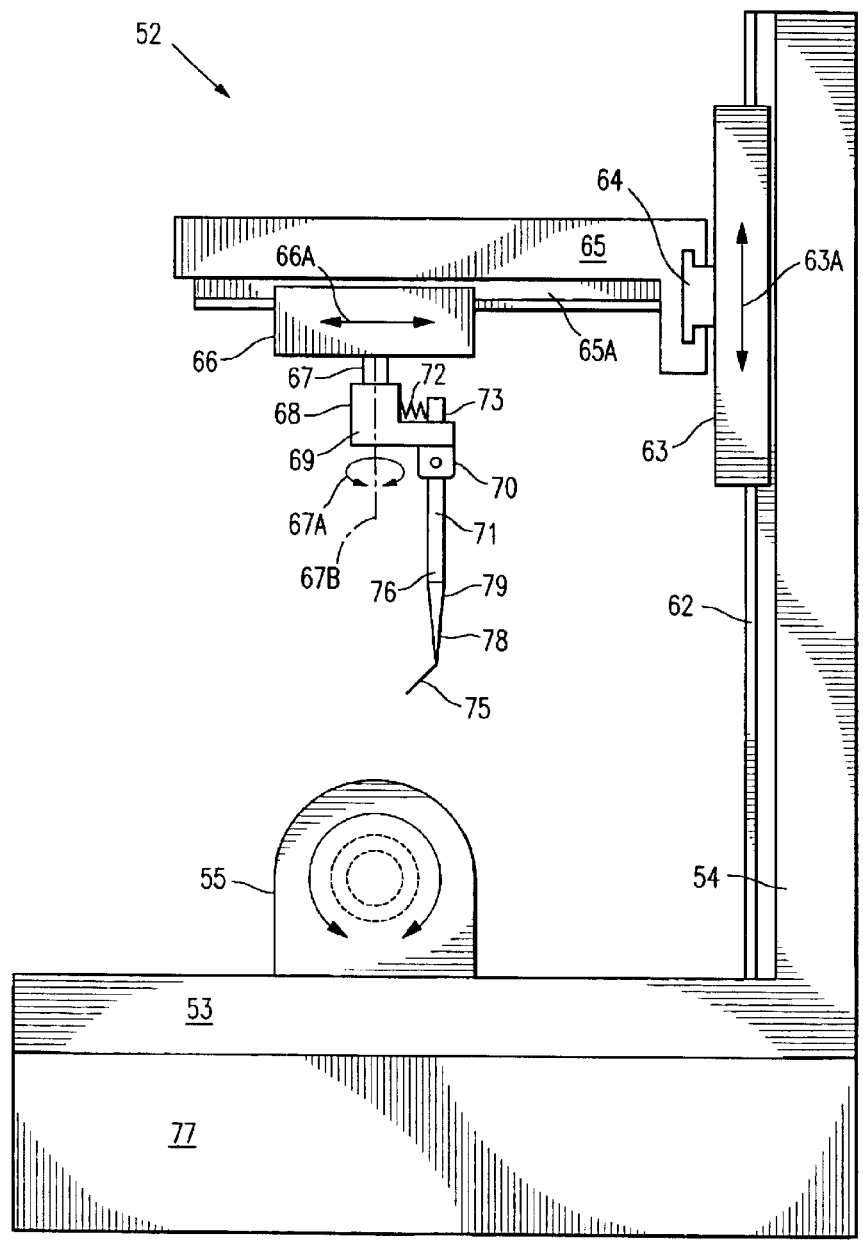
FIG. 13A is a side view from the right hand side of a five axis seam forming apparatus.
Figure 13B:
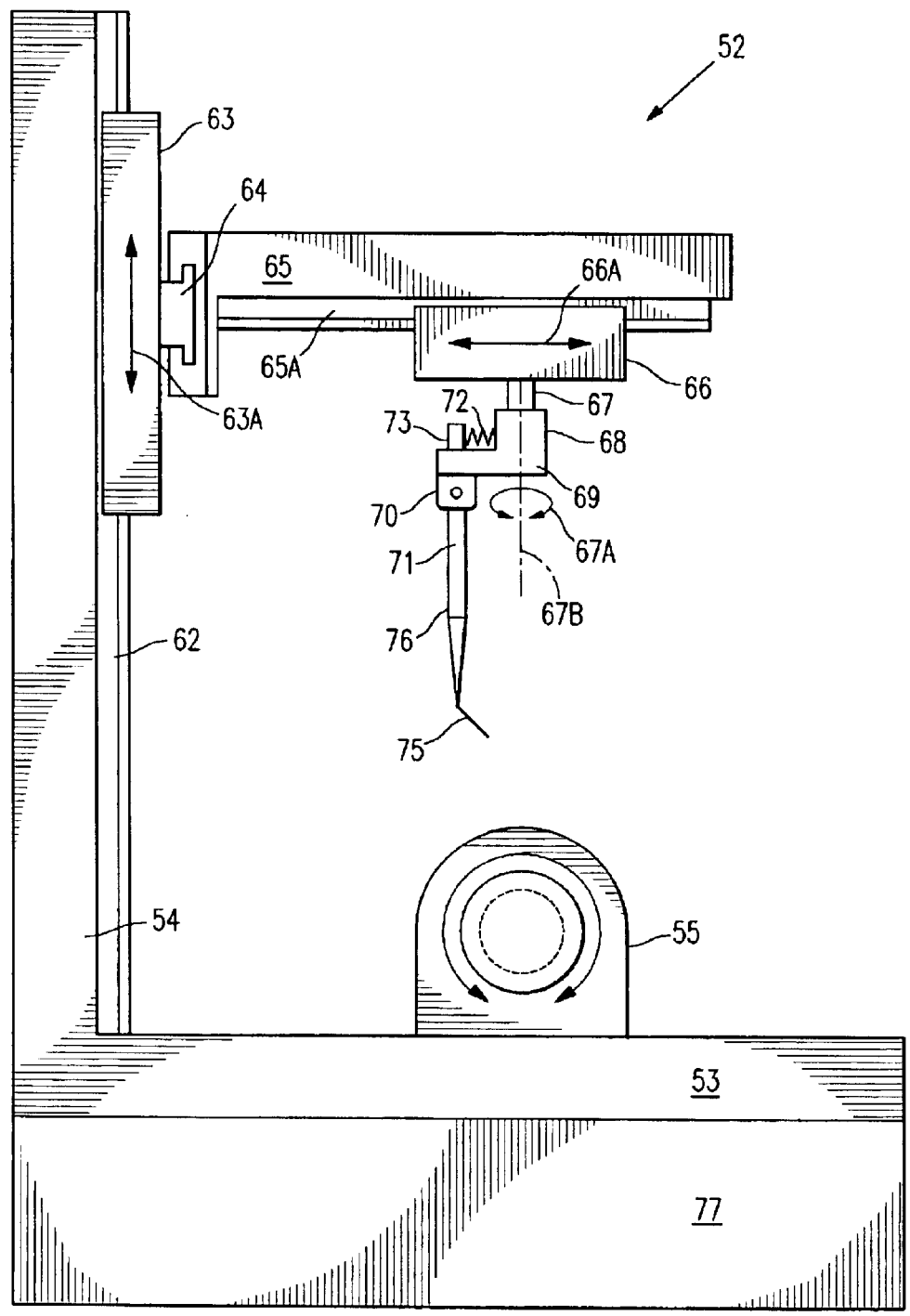
FIG. 13B is a side view from the left hand side of a five axis seam forming apparatus.
Figure 13C:
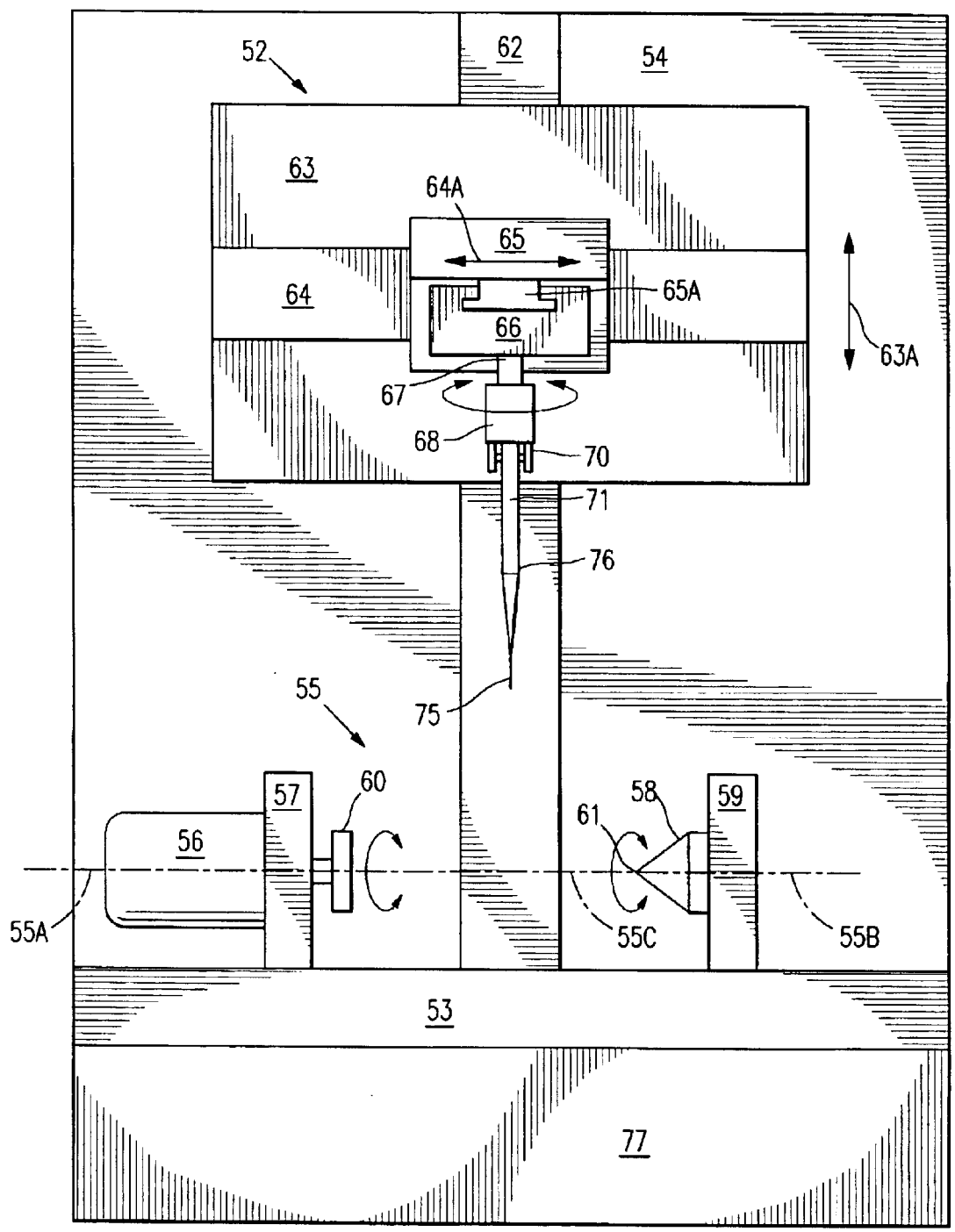
FIG. 13C is a front view of the five axis seam forming apparatus of FIGS. 13A and 13B.
Figure 13D:
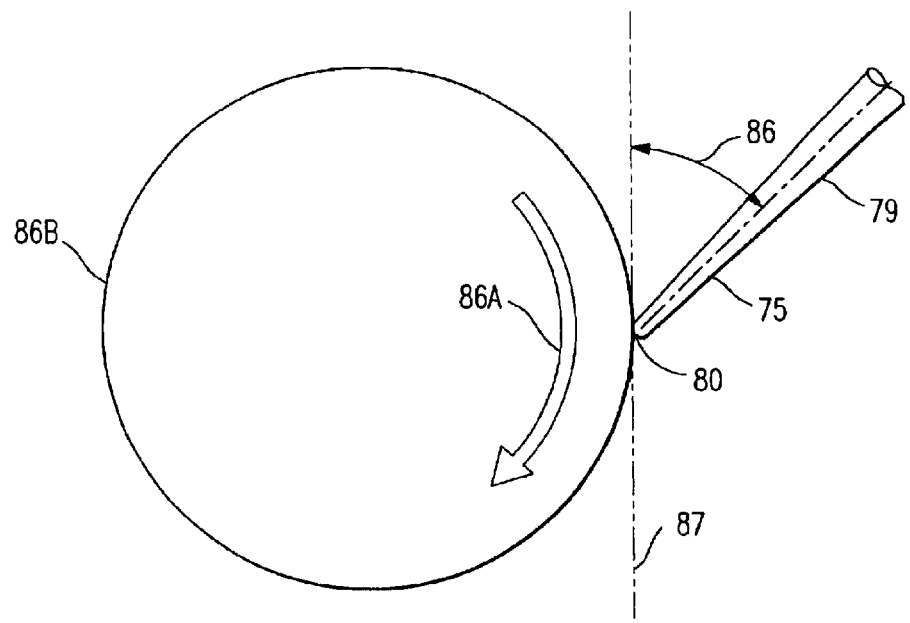
FIG. 13D shows a stylus tip in contact with a transverse cross sectioned view of a cylindrical shape forming member with an axis of the stylus tip oriented at an angle with the tangent of the shape forming member at the point of contact therebetween.

FIG. 13D illustrates an enlarged view of a stylus tip 75 applied to a rotating cylindrical surface 86B with the surface rotating in a counterclockwise direction as indicated by arrow 86A. The cylindrical surface can support one or more layers of fusible material (not shown) between the distal extremity 80 of the stylus tip 75 and the surface 86B which require seam to be formed therein. The stylus tip 75 has a longitudinal axis that forms an angle 86 with a tangent to the surface of the cylindrical surface indicated by dashed line 87. Although not necessary, we have found it useful to have the object in contact with the stylus tip 75 rotating or moving in a direction as show in FIG. 13D, relative to angle 86 in order to prevent chatter of the configuration or distortion of fusible material on the surface 86A. In one embodiment, angle 86 may range from about 5 to about 60 degrees; specifically, from about 10 to about 20 degrees. It is also useful if the distal extremity 80 of the stylus tip 75 has a smooth surface and is radiused. A suitable radius for one embodiment may range from about 0.01 to about 0.030 inch; specifically, from about 0.015 to about 0.02 inch.

Figure 13E:
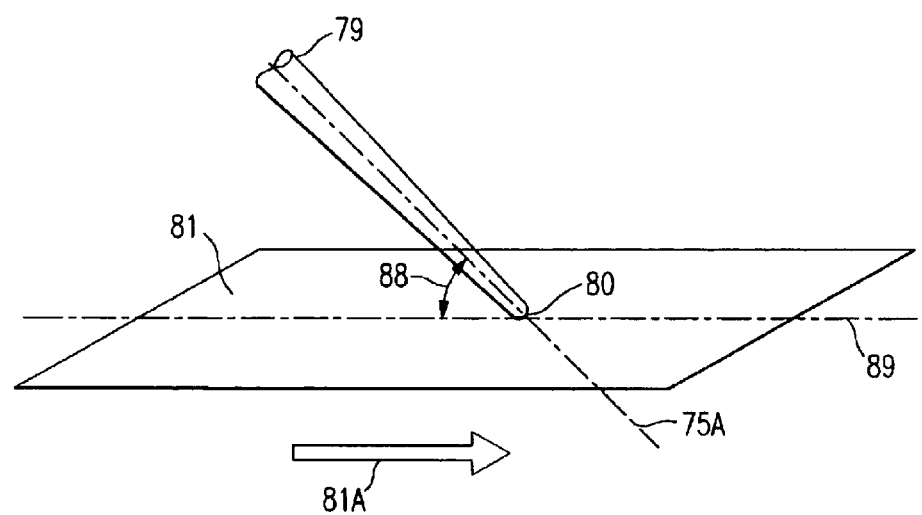
FIG. 13E illustrates a stylus tip in contact with a plurality of layers of fusible material in a substantially flat configuration with the longitudinal axis of the stylus tip at an angle with respect to a line which is orthogonal to the surface of the layers.

FIG. 13E shows a similar relationship between a stylus tip 75 and hard surface 81. Surface 81 may have one or more layers of fusible material (not shown) disposed thereon between distal extremity 80 and surface 81. A longitudinal axis 75A of stylus tip 75 forms an angle 86 with the dashed line 89 that is parallel to surface 81. Angle 88 in this embodiment should range from about 5 to about 60 degrees; specifically, from about 10 to about 20 degrees, so to ensure smooth relative motion between surface 81 and tip 75. The surface 81 is shown moving relative to the stylus tip 75 in the direction indicated by arrow 81A.

The pressure exerted by the extremity 80 of stylus tip 75 on the material being processed is another parameter that can affect the quality of a seam formed in layers of fusible material. In one embodiment in which the stylus tip is heated, the pressure exerted by the distal extremity 80 of the stylus tip 75 may range from about 100 to about 6,000 pounds per square inch (psi); specifically, from about 300 to about 3,000 psi. The speed of the heated stylus 75 relative to the material being processed, such as that of graft body section 15, may range from about 0.2 to about 10 mm per second, specifically, from about 0.5 to about 1.5 mm per second. The temperature of the distal extremity 80 of the heated stylus tip 75 in this embodiment may range from about 320 to about 550 degrees Celsius; specifically, about 380 to about 420 degrees Celsius.

Seam formation for ePTFE normally occurs by virtue of the application of both heat and pressure. The temperatures at the tip of the heated stylus 75 during such seam formation are generally above the melting point of highly crystalline ePTFE, which may range be from about 327 to about 340 degrees Celsius, depending in part on whether the material is virgin material or has previously been sintered). In one embodiment, the stylus tip temperature for ePTFE welding and seam formation is about 400 degrees Celsius. Pressing such a heated tip 75 into the layers of ePTFE against a hard surface such as the outside surface of the shape forming mandrel) compacts and heats the adjacent layers to form a seam with adhesion between at least two of, if not all, the layers. At the seam location and perhaps some distance away from the seam, the ePTFE generally transforms from an expanded state with a low specific gravity to a non-expanded state (i.e., PTFE) with a relatively high specific gravity. Some meshing and entanglement of nodes and fibrils of adjacent layers of ePTFE may occur and add to the strength of the seam formed by thermal-compaction. The overall result of a well-formed seam between two or more layers of ePTFE is adhesion that can be nearly as strong or as strong as the material adjacent the seam. The microstructure of the layers may change in the seam vicinity such that the seam will be impervious to fluid penetration.

It is important to note that a large number of parameters determine the proper conditions for creating the fusible material seam, especially when that material is ePTFE. Such parameters include, but are not limited to, the time the stylus tip 75 is in contact with the material (or for continuous seams, the rate of tip movement), the temperature (of the tip extremity 80 as well as that of the material, the underlying surface 81, and the room), tip contact pressure, the heat capacity of the material, the mandrel, and the other equipment, the characteristics of the material (e.g. the node and fibril spacing, etc.), the number of material layers present, the contact angle between the tip extremity 80 and the material, the shape of the extremity 80, etc. Knowledge of these various parameters is useful in determining the optimal combination of controllable parameters in forming the optimal seam. And although typically a combination of heat and pressure is useful in forming an ePTFE seam, under proper conditions a useful seam may be formed by pressure at ambient temperature (followed by elevation to sintering temperature); likewise, a useful seam may also be formed by elevated temperature and little-to-no applied pressure.

For example, we have created seams in ePTFE that formed an intact, inflatable cuff by the use of a clamshell mold that presented an interference fit on either side of a cuff zone for the ePTFE. The application of pressure alone without using an elevated temperature prior to sintering formed a seam sufficient to create a working cuff.

Figure 13F:
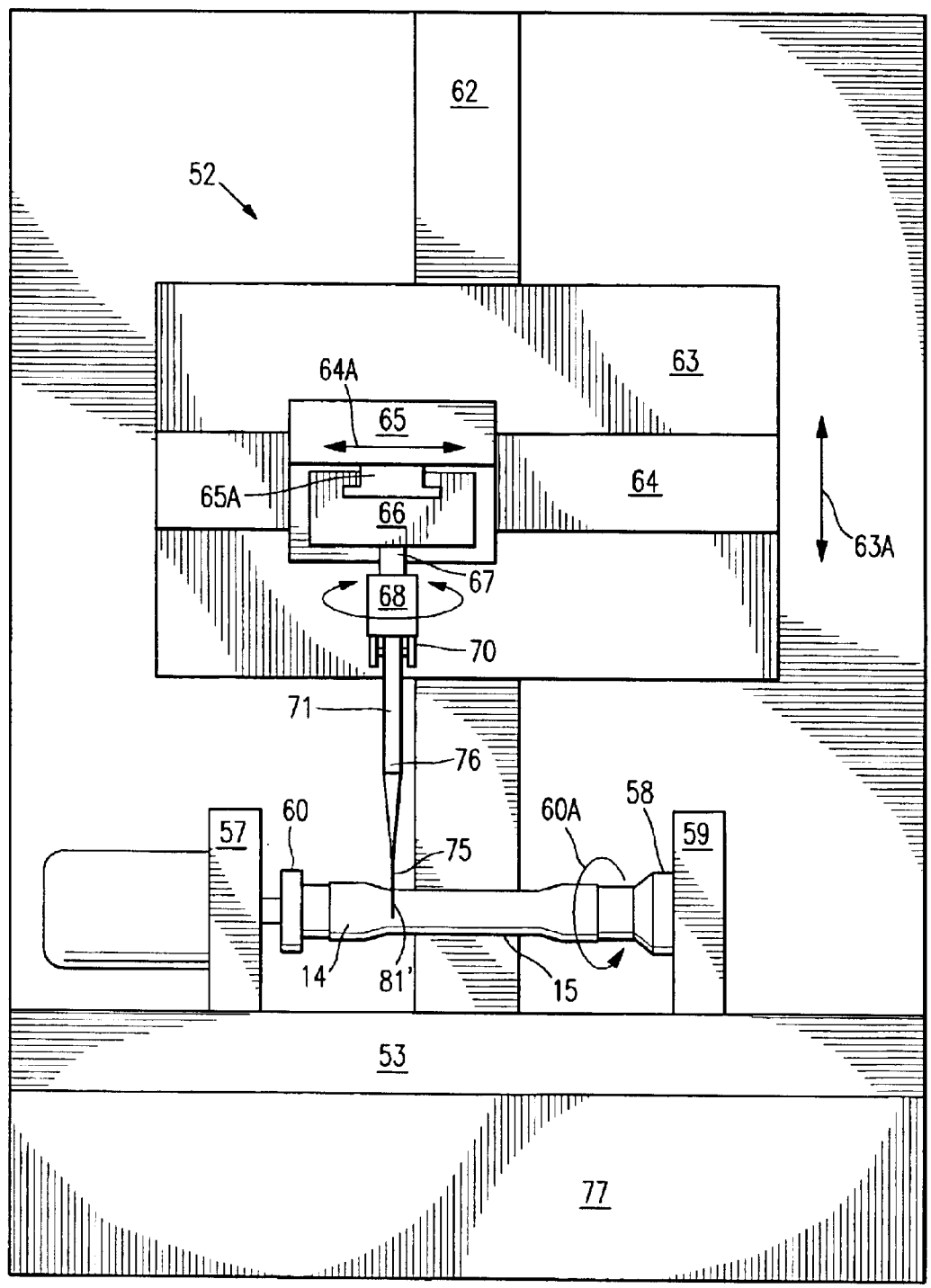
FIG. 13F is a front view of the seam forming apparatus with a shape forming mandrel and a graft body section on the shape forming mandrel positioned in the chuck of the seam forming member mount system.

FIG. 13F depicts a front view of the seam forming apparatus 52 with a shape forming mandrel 14 secured to the chuck 60 and the live center unit 58. The distal extremity of the heated stylus tip 75 is in contact with the graft body section 15 which is disposed on the shape forming mandrel 14. The chuck 60 is turning the shape forming mandrel 14 and graft body section 15 in the direction indicated by the arrow 60A to form a seam 81 between the layers of fusible material of the graft body section 15.

Figure 13G:
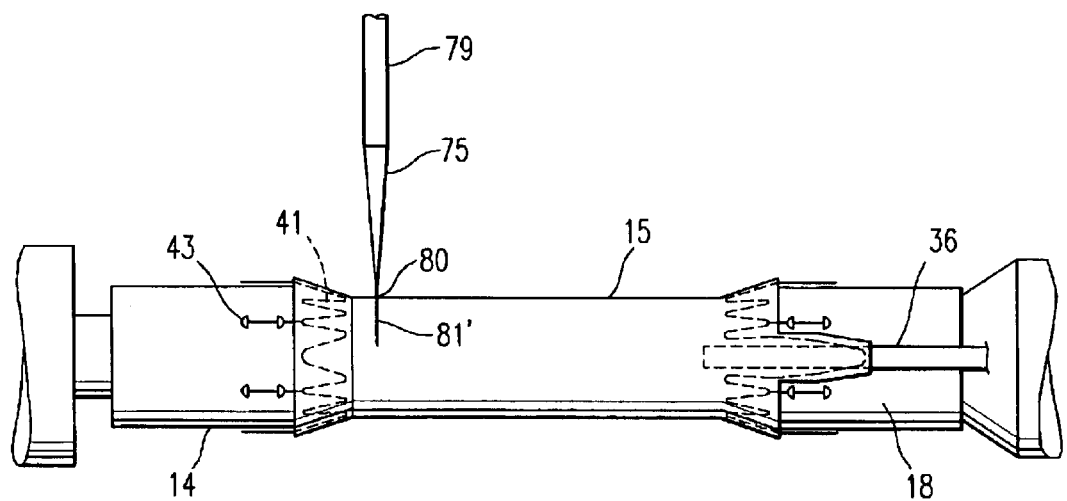
FIG. 13G illustrates a distal extremity or tip of a stylus in contact with the layers of fusible material of the graft body section.
Figure 13H:
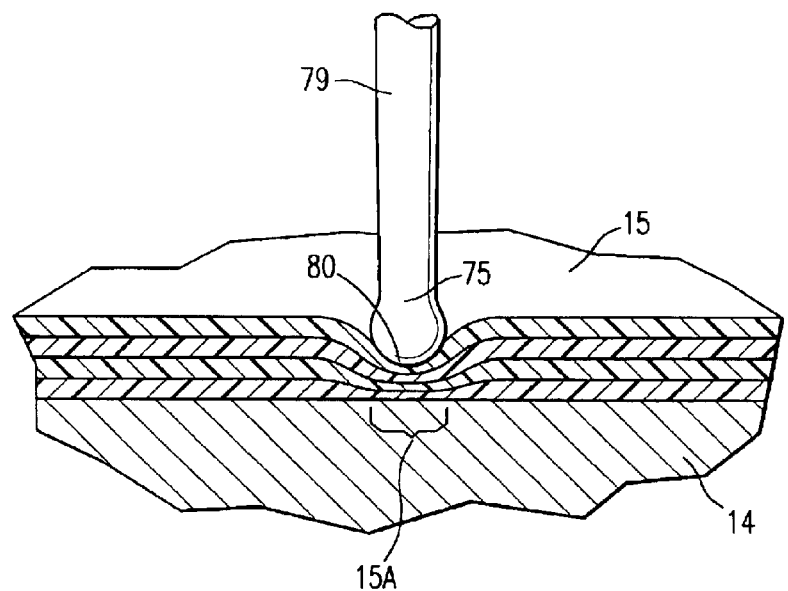
FIG. 13H illustrates the tip of a stylus in contact with layers of fusible material of the graft body section, forming a seam in the layers.

FIGS. 13G and 13H illustrate an enlarged view of the heated stylus tip 75 in contact with the graft body section 15 in the process of creating one ore more seams 81 which are configured to form elongate inflatable channels 82 in the graft body section 15. The term "inflatable channels" may generally be described herein as a substantially enclosed or enclosed volume between layers of fusible material on a graft or graft section, and in some embodiments, in fluid communication with at least one inlet port for injection of inflation material. The enclosed volume of an inflatable channel or cuff may be zero if the inflatable cuff or channel is collapsed in a non-expanded state. The enclosed volume of an inflatable channel may or may not be collapsible during compression or compacting of the graft body section 15.

FIG. 13H is an enlarged view in section of the distal extremity 80 of the heated stylus tip 75 in contact with layers of fusible material of graft body section 15. The layers of fusible material are being heated and compressed to form a bond 15A therebetween. The seam forming apparatus can position the distal extremity 80 at any desired location on the graft body section 15 by activation of one or more of the five motors controlled by the components in the control unit housing 77. Each of the five motors controls relative movement between graft body section 15 and distal extremity 80 in one degree of freedom. Thus, the distal extremity 80 may be positioned above the surface of the graft body section 15, as shown in FIG. 13C, and brought to an appropriate temperature for seam formation, as discussed above, by resistive heating or any other appropriate method. Once extremity 80 has reached the target temperature, it can be lowered by activation of the motor which controls movement of the vertical car. The extremity 80 can be lowered and horizontally positioned by other control motors until it contacts the graft body section in a desired predetermined position on graft body section 15, as shown in FIG. 13F.

Once distal extremity 80 makes contact with graft body section 15 with the proper amount of pressure, it begins to form a seam between the layers of the fusible material of the graft body section as shown in FIG. 13H. The pressure or force exerted by the extremity 80 on the graft body section may be determined by the spring constant and amount of deflection of torsion spring 72 shown in FIGS. 13A and 13B; generally, we have found a force at the extremity 80 ranging from about 0.2 to about 100 grams to be useful. As the seam formation process continues, the surface of graft body section 15 may be translated with respect to the distal extremity 80 while desirably maintaining a fixed, predetermined amount of pressure between the distal extremity 80 and the layers of fusible material of the graft body section. The CPU (or an equivalent device capable of controlling the components of apparatus 52) of the control unit housing 77 may be programmed, for instance, a mathematical representation of the outer surface contour of any known shape forming member or mandrel.

The CPU is thereby able to control movement of the five motors of apparatus 52, so that distal extremity 80 may follow the contour of the shape forming member while desirably exerting a fixed predetermined amount of pressure the layers of fusible material disposed between the distal extremity 80 and the shape forming member. While seam formation is taking place, the pressure exerted by the distal extremity 80 on the shape forming member may be adjusted dynamically. The extremity 80 may also be lifted off the graft body section and shape forming member in locations where there is a break in the desired seam pattern. Once distal extremity 80 is positioned above the location of the starting point of the next seam following the break, the extremity 80 may then be lowered to contact the layers of fusible material, reinitiating the seam formation process.

Use of the seam forming apparatus 52 as described herein is but one of a number of ways to create the desired seams in the graft body section 15 of the present invention. Any suitable process and apparatus may be used as necessary and the invention is not so limited. For instance, seams may also be formed in a graft body section 15 by the use of a fully or partially heated clamshell mold whose inner surfaces contain raised seam-forming extensions. These extensions may be configured and preferentially or generally heated so that when the mold halves are closed over a graft body section 15 disposed on a mandrel, the extensions apply heat and pressure to the graft body section directly under the extensions, thereby "branding" a seam in the graft body section in any pattern desired and in a single step, saving much time over the technique described above in conjunction with seam forming apparatus 52.

If the fusible material comprises ePTFE, it is also possible to infuse or wick an adhesive (such as FEP or PFA) or other material into the ePTFE layers such that the material flows into the fibril/node structure of the ePTFE and occupies the pores thereof. Curing or drying this adhesive material will mechanically lock the ePTFE layers together through a continuous or semi-continuous network of adhesive material now present in and between the ePTFE layers, effectively bonding the layers together.

Figure 14:
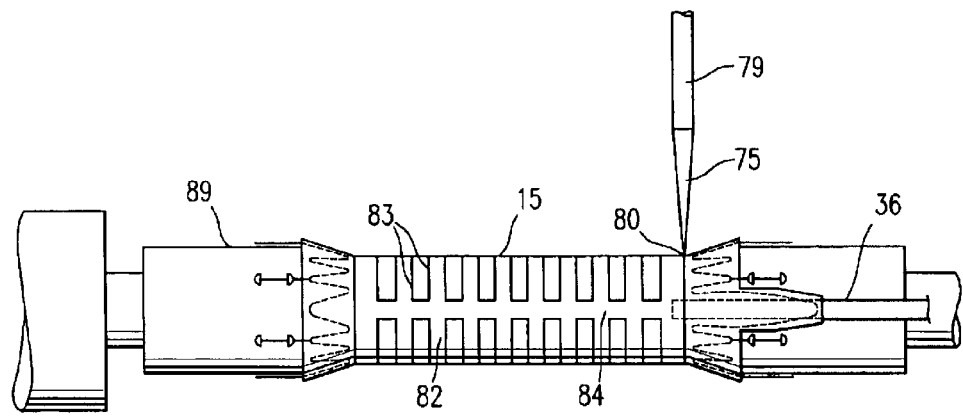
FIG. 14 shows inflation channels being formed in the layers of fusible material on the shape forming mandrel by the seam forming apparatus stylus tip.
Figure 15:
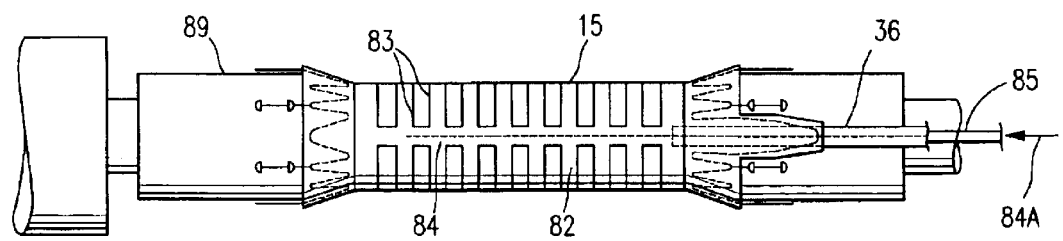
FIG. 15 shows the graft body section with the channel formation complete and pressurized fluid being injected into an inflatable channel network in order to expand the inflatable channels.

FIG. 14 illustrates a substantially completed set of seams 81 formed in the layers of fusible material of the graft body section 15, which seams form inflatable channels 82. FIG. 15 illustrates graft body section 15 as fluid (such as compressed gas) is injected into the inflation line 36 and in turn into the inflatable channel network 84 of body section 15, as shown by arrow 84A. The fluid is injected to pre-stress the inflatable channels 82 of body section 15 and expand them outward radially. The fluid may be delivered or injected through an optional elongate gas containment means having means for producing a permeability gradient in the form of a manifold or pressure line 85. The pressure line 85 shown in FIG. 15 has a configuration with an input (not shown) located outside the inflation line and a plurality of outlet apertures or orifices (not shown) that may be configured to provide an even distribution of pressure within the inflatable channel network 84. Other fluid injection schemes and configurations are of course possible.

Because ePTFE is a porous or semi-permeable material, the pressure of exerted by injected fluids such as pressurized gas tends to drop off or diminish with increasing distance away from the outlet apertures or orifices (not shown) of manifold or pressure line 85. Therefore, in some embodiments, pressure line 85 may comprise apertures or orifices (not shown) which, when disposed in graft body section 15, progressively increases in size as one moves distally along the pressure line towards the proximal end 17 graft body section 15 in order to compensate for a drop in pressure both within the inflatable channel network 84 and within the manifold or pressure line 85 itself.

Figure 16A:
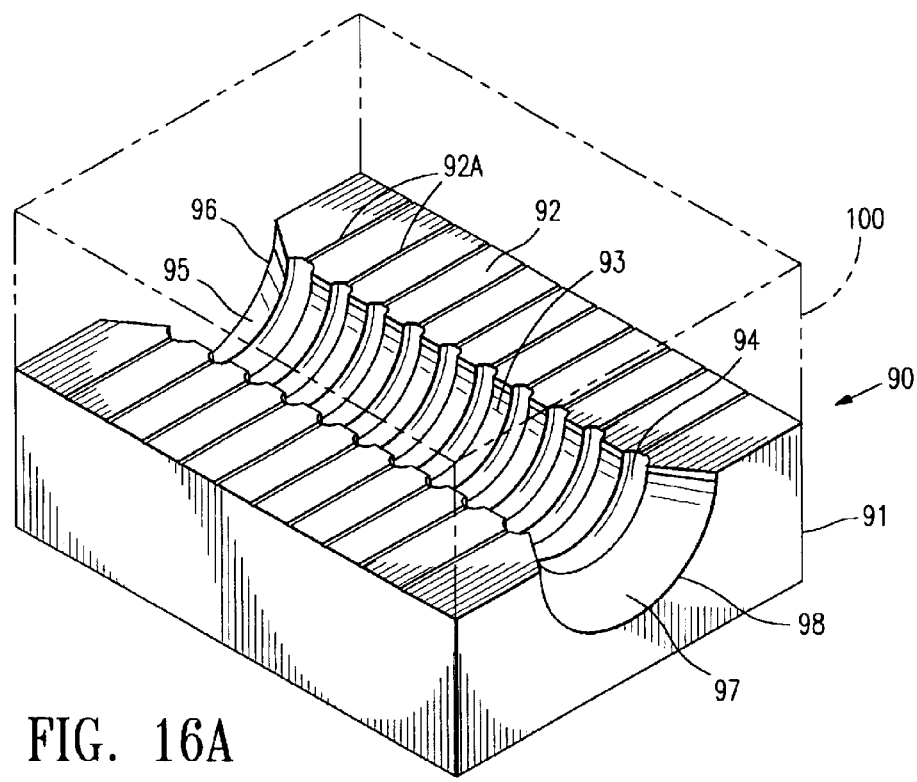
FIG. 16A illustrates one half of an embodiment of a two-piece mold for use during expansion of the inflatable channels formed by the seam forming apparatus.

Once some or all of the inflatable channels 82 have been pre-expanded or pre-stressed, the graft body section 15 and shape forming mandrel assembly 89 may then be positioned within an outer constraint means in the form of a mold to facilitate the inflatable channel expansion and sintering process. One half of a mold 90 suitable for forming an embodiment of a graft body section 15 such as that shown in FIG. 15 is illustrated in FIG. 16A. A mold half body portion 91 is one of two pieces of mold 90. A mold similar to mold 90 could be made from any number of mold body portions configured to fit together. For example, a mold 90 could be designed from three, four, five or more mold body portions configured to fit together to form a suitable main cavity portion 93 for maintaining the shape of graft body section 15 during channel expansion and sintering. For certain configurations, a one-piece mold may be used.

Mold body portion 91 has a contact surface 92 and a main cavity portion 93. Main cavity portion 93 has an inside surface contour configured to match an outside surface contour of the graft body section with the inflatable channels in an expanded state. Optional exhaust channels 92A may be formed in contact surface 92 and provide an escape flow path for pressurized gas injected into the inflatable channel network 84 during expansion of the inflatable channels 82.

Figure 16B:
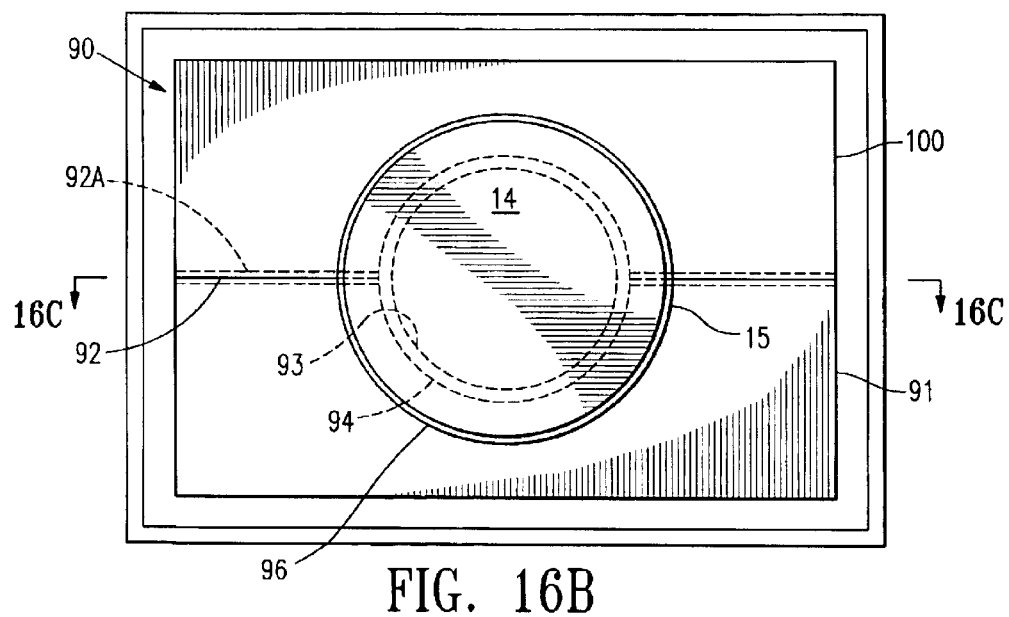
FIG. 16B is an end view showing the shape forming mandrel and graft body section within both halves of the mold.

The main cavity portion 93 of the FIGS. 16A–16B embodiment is substantially in the shape of a half cylinder with circumferential channel cavities 94 for forming the various inflatable channels 82 of graft body section 15. Cavity 93 has a first tapered portion 95 at the proximal end 96 of mold 90 and a second tapered portion 97 at the mold distal end 98. FIG. 16B shows an end view of mold 90 with the two mold body portions 91 and 100 pressed together with the assembly of the graft body section 15 and shape forming mandrel 14 disposed mold cavity 93.

Figure 16C:
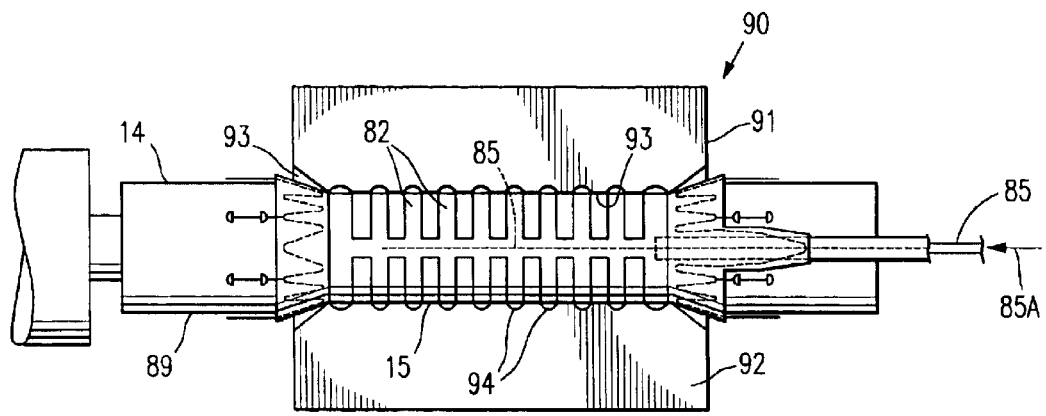
FIG. 16C shows the graft body section and shape forming mandrel disposed within the mold cavity (with one half of the mold removed for clarity of illustration) with a fluid being injected into the inflatable channels of the graft body section in order to keep the inflatable channels in an expanded state during the fixing or sintering of the fusible material.

FIG. 16C shows the assembly of the graft body section 15 and shape forming mandrel 14 disposed within mold 90, with the circumferential inflatable channels 82 of the graft body section 15 aligned with the circumferential channel cavities 94 of the main cavity portion 93. One mold body portion 100 of mold 90 is not shown for the purpose of clarity of illustration. A pressurized fluid Indicated as being delivered or injected into manifold or pressure line 85 by arrow 85A.

Figure 17:
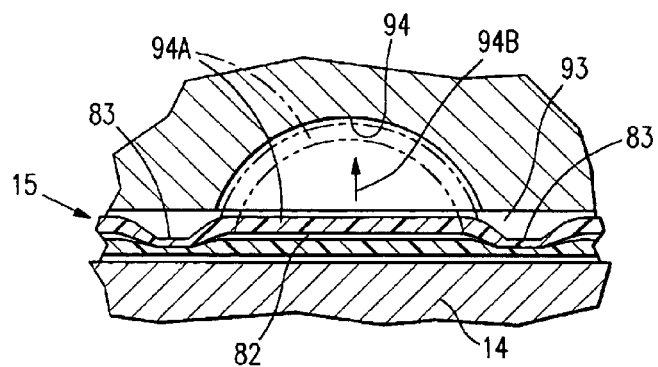
FIG. 17 illustrates an outer layer or layers of fusible material being forced into the mold cavity of a portion of the mold by pressurized fluid as indicated by the dotted line.

FIG. 17 illustrates by the phantom lines how the outer layers 94A of circumferential inflatable channel 82 of the fusible material of a graft body section 15 are expanded into the circumferential channel cavity 94 of mold cavity 93. The direction of the expansion of the outer layers 94A to the position indicated by the phantom lines is indicated by arrow 94B. A cross sectional view of the seams 83 of the circumferential inflatable channel 82 is shown in FIG. 17 as well.

While the graft body section network of inflatable channels 84 is in an expanded state by virtue of pressurized material being delivered or injected into pressure line 85, the entire assembly may be positioned within an oven or other heating device (not shown) in order to bring the fusible material of graft body section 15 to a suitable temperature for an appropriate amount of time in order to fix or sinter the fusible material. In one embodiment, the fusible material is ePTFE and the sintering process is carried out by bringing the fusible material to a temperature of between about 335 and about 380 degrees Celsius; specifically, between about 350 and about 370 degrees Celsius. The mold may then be cooled and optionally quenched until the temperature of the mold drops to about 250 degrees Celsius. The mold may optionally further be quenched (for handling reasons) with ambient temperature fluid such as water. Thereafter, the two halves 91 and 100 of mold 90 can be pulled apart, and the graft assembly removed.

The use of mold 90 to facilitate the inflatable channel expansion and sintering process is unique in that the mold cavity portion 93 acts as a backstop to the graft body section so that during sintering, the pressure created by the injected fluid that tends to expand the inflatable channels outward is countered by the restricting pressure exerted by the physical barrier of the surfaces defining the mold cavity 93. In general terms, therefore, it is the pressure differential across the inflatable channel ePTFE layers that in part defines the degree of expansion of the channels during sintering. During the sintering step, the external pressure exerted by the mold cavity surface competes with the fluid pressure internal to the inflatable channels (kept at a level to counteract any leakage of fluid through the ePTFE pores at sintering temperatures) to provide an optimal pressure differential across the ePTFE membrane(s) to limit and define the shape and size of the inflatable channels.

Based on this concept, we have found it possible to use alternatives to a mold in facilitating the inflatable channel expansion process. For instance, it is possible inject the channel network with a working fluid that does not leak through the ePTFE pores and to then expand the network during sintering in a controlled manner, without any external constraint. An ideal fluid would be one that could be used within the desired ePTFE sintering temperature range to create the necessary pressure differential across the inflatable channel membrane and the ambient air, vacuum, or partial vacuum environment so to control the degree of expansion of the channels. Ideal fluids are those that possess a high boiling point and lower vapor pressure and that do not react with ePTFE, such as mercury or sodium potassium. In contrast, the network of inflatable channels 84 can also be expanded during the fixation process or sintering process by use of vapor pressure from a fluid disposed within the network of Inflatable channels 84. For example, the network of inflatable channels 84 can be filled with water or a similar fluid prior to positioning assembly in the oven, as discussed above. As the temperature of the graft body section 15 and network of inflatable channels 84 begins to heat, the water within the network of inflatable channels 84 begins to heat and eventually boil. The vapor pressure from the boiling water within the network of inflatable channels 84 will expand the network of inflatable channels 84 provided the vapor is blocked at the inflation line 85 or otherwise prevented from escaping the network of inflatable channels.

Figure 18:
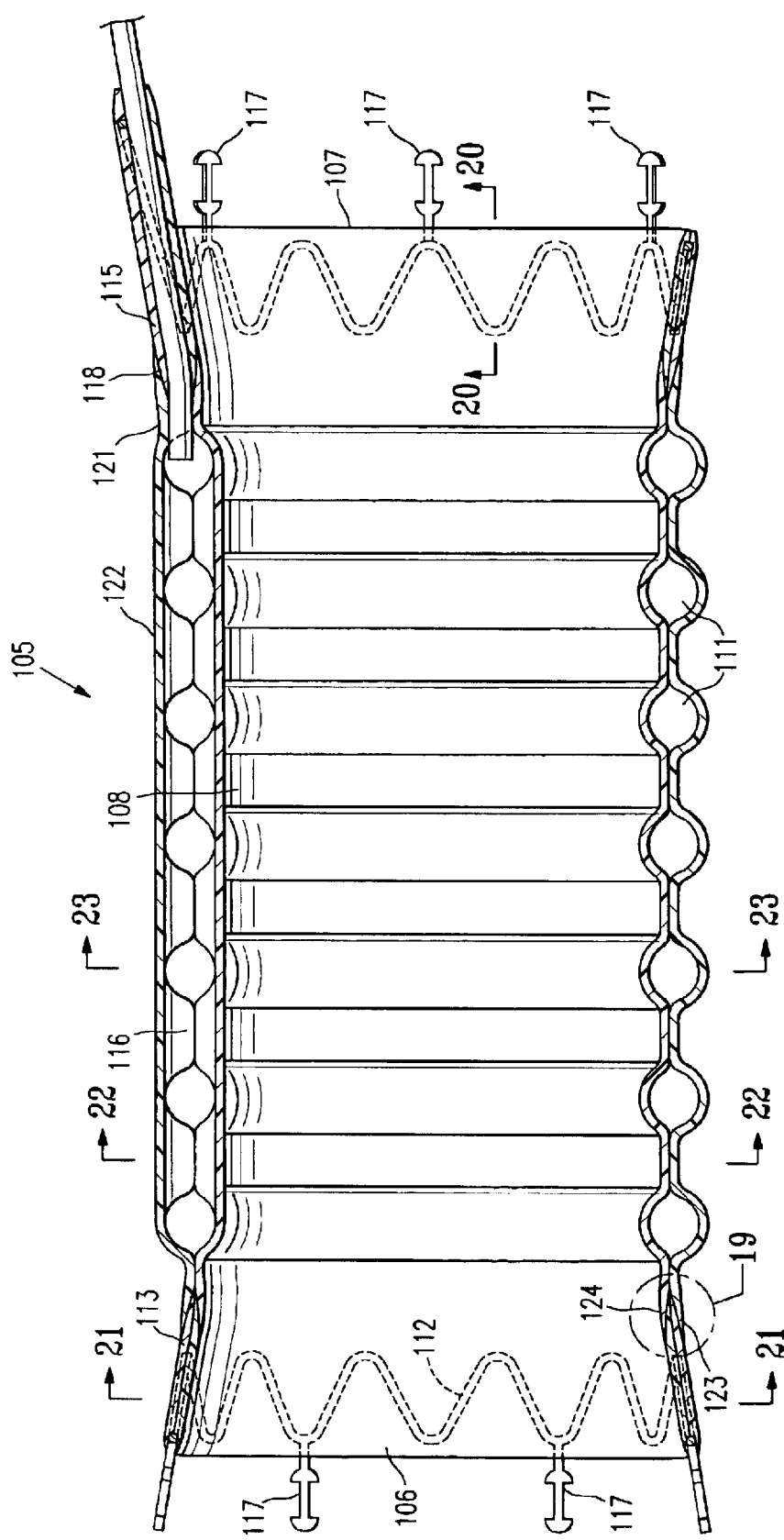
FIG. 18 is an elevational view in partial section of an embodiment of an by inflatable endovascular graft of the present invention.

FIG. 18 shows an elevational view in partial longitudinal section of an endovascular graft assembly 105 manufactured by the methods and with the apparatus described above. Endovascular graft assembly 105 comprises a graft body section 108 with a proximal end 106, a distal end 107, and circumferentially oriented inflatable channels 111 shown in an expanded state. A longitudinal inflatable channel 116 fluidly communicates with the circumferential inflatable channels 111.

An expandable member in the form of a proximal connector member 112 is shown embedded between proximal end wrap layers 113 of fusible material. An expandable member in the form of a distal connector member 114 is likewise shown embedded between distal end wrap layers 115 of fusible material. The proximal connector member 112 and distal connector member 114 of this embodiment are configured to be secured or connected to other expandable members which may include stents or the like, which are not shown. In the embodiment of FIG. 18, such a connection may be accomplished via connector elements 117 of the proximal and distal connector members 112 and 114, which extend longitudinally outside of the proximal and distal end wrap layers 113 and 115 away from the graft body section 108.

The FIG. 18 embodiment of the present invention features junction 118 between the distal end wrap layers 115 of fusible material and the layers of fusible material of a distal end 121 of the graft assembly main body portion 122. There is likewise a junction 123 between the proximal end wrap layers 113 and the layers of fusible material of a proximal end 124 of the graft assembly main body portion 122. The junctions 118 and 123 may be tapered, with overlapping portions that are bound by sintering or thermomechanical compaction of the end wrap layers 113 and 115 and layers of the main body portion 122. This junction 123 is shown in more detail in FIG. 19.

Figure 19:
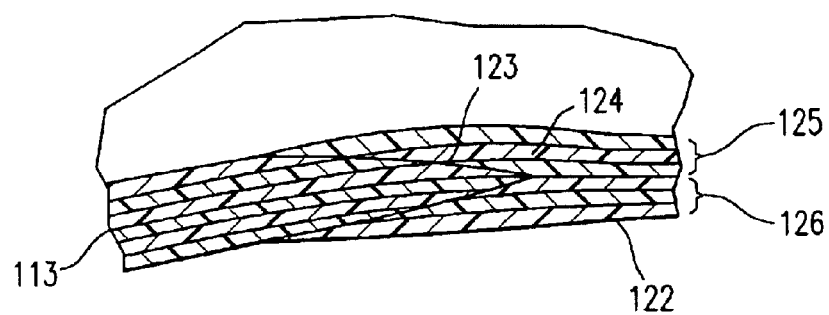
FIG. 19 is an enlarged view of the graft of FIG. 18 taken at the dashed circle indicated by numeral 19 in FIG. 18.

In FIG. 19, six proximal end wrap fusible material layers 113 are disposed between three fusible material inner layers 125 and three fusible material outer layers 126 of the main body portion proximal end 124.

Figure 20:
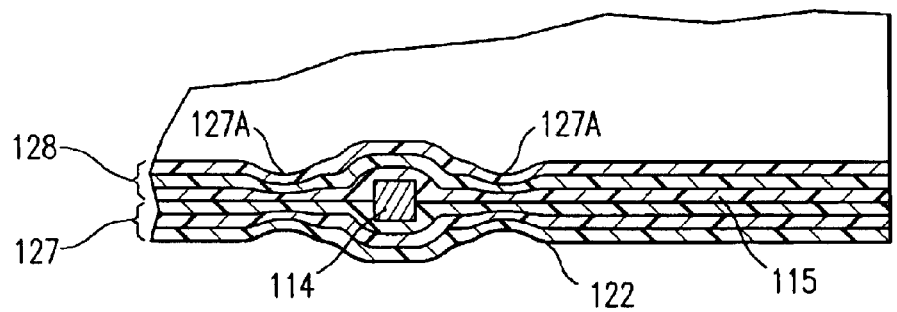
FIG. 20 is an enlarged view in section taken along lines 20—20 in FIG. 18.
Figure 21:
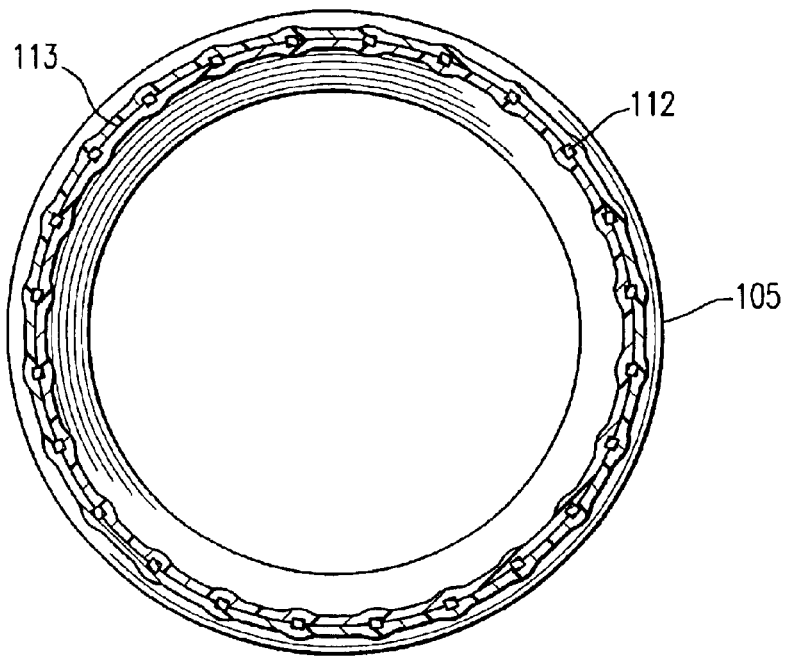
FIG. 21 is a transverse cross sectional view of the graft of FIG. 18 taken along lines 21—21 in FIG. 18.

FIG. 20 illustrates a sectional view of a portion of the distal connector member 114 disposed within the distal end wrap layers 115 of fusible material. Connector member 114 is disposed between three outer layers 127 of fusible material and three inner layers 128 of fusible material. Optional seams 127A, formed by the methods discussed above, are disposed on either side of distal connector member 114 and mechanically capture the connector member 114. FIG. 21 likewise is a transverse cross sectional view of the proximal connector member 112 embedded in the proximal end wrap layers 113 of fusible material.

Figure 22:
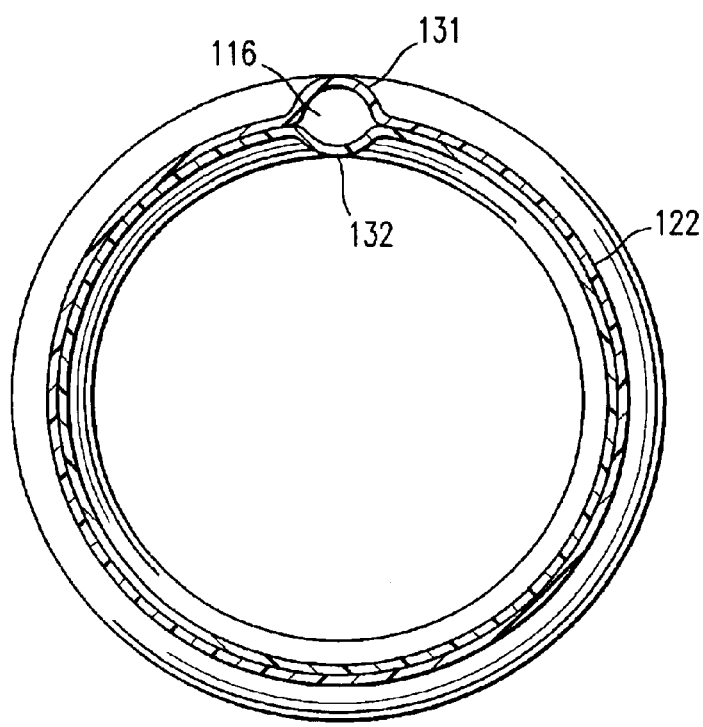
FIG. 22 is a transverse cross sectional view of the graft of FIG. 18 taken along lines 22—22 in FIG. 18.
Figure 23:
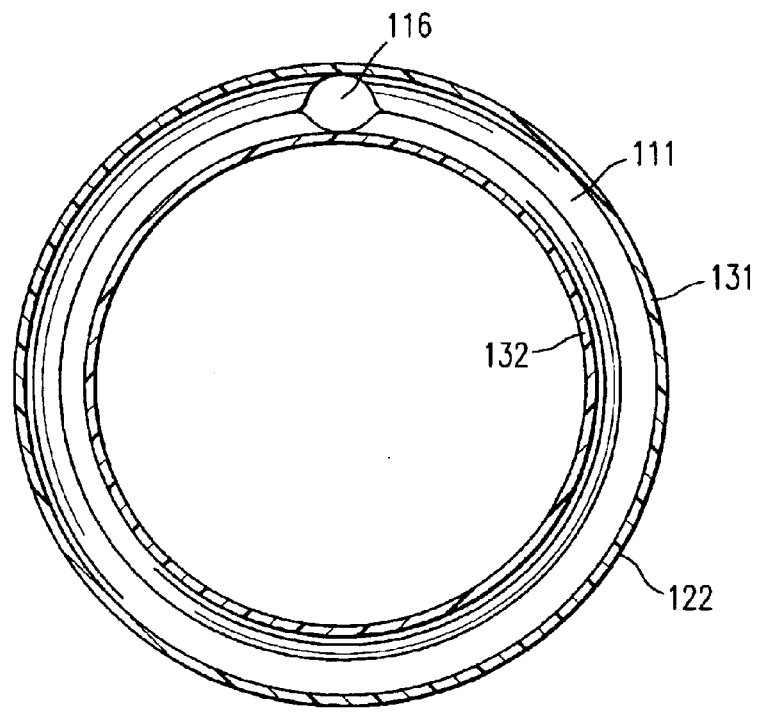
FIG. 23 is a transverse cross sectional view of the graft of FIG. 18 taken along lines 23—23 in FIG. 18.

FIG. 22 illustrates a transverse cross section of the longitudinal inflatable channel 116 formed between main body portion 122 outer layers 131 and the main body portion 122 inner layers 132. FIG. 23 is a transverse cross section of graft main body portion 122 showing a circumferential inflatable channel 111 in fluid communication with longitudinal inflatable channel 116. The circumferential inflatable channel 111 is formed between the outer layers 131 of fusible material of main body portion 122 and inner layers 132 of fusible material of main body portion 122.

Figure 24:
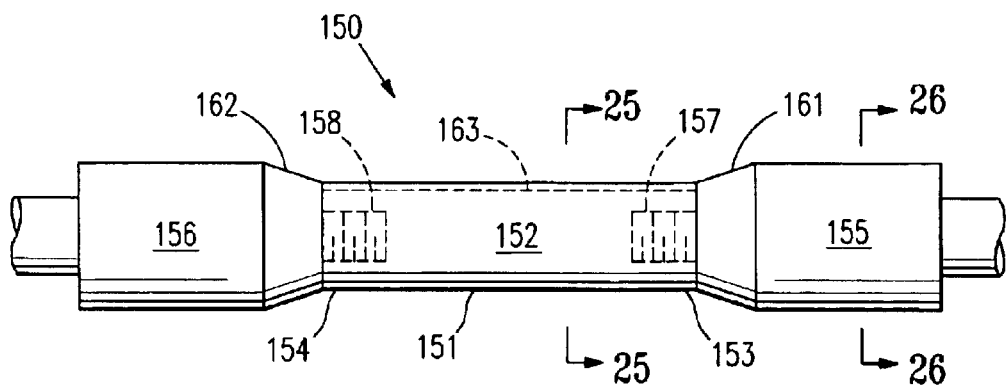
FIG. 24 is an elevational view of an embodiment of a shape forming mandrel with a pressure line recess.

FIG. 24 shows an alternate embodiment of an interior surface support means in the form of an elongate mandrel 150 for shape forming an endovascular graft or section thereof. The mandrel 150 has an outer surface contour 151 configured to support an inside surface of an graft section and is substantially cylindrical in configuration. The mandrel 150 has a middle section 152 with a first end 153 and a second end 154. Additionally, a mandrel first end section 155 is disposed at first end 153 of middle section and a mandrel second end section 156 is disposed at second end 154 of middle section 152. First and second end sections 155 and 156 typically have an outer transverse dimension, at least a portion of which is larger than the outer transverse dimension of middle section 152. First end section 155 is removably secured to the first end 153 of middle section 152 by threaded portion 157. Alternatively, first end section 155 may be removably secured by any other suitable mechanism or means such as attached by set screws, interlocking mechanisms or the like. In some embodiments second end section 156 may be removably attached to second end 154 of the shape forming mandrel 150 by threaded portions 158 or alternate securement mechanisms. Middle section 152 of mandrel 150 will typically range in length from about 50 to about 150 mm, specifically from about 75 to about 100 mm, and typically has an outer transverse dimension from about 5 to about 50 mm; specifically from about 15 to about 25 mm. Typically first and second end sections 155 and 156 may have a tapered portion 161 and 162 adjacent first and, second ends 153 and 154 of middle section 152, respectively. First end section 155 is substantially cylindrical in configuration and typically has an outer transverse dimension of about 15 to about 40 mm, such as about 20 to about 30 mm. Second end section 156 may have a similar configuration. Typically middle section 152, first end section 155 and second end section 156 are substantially circular or elliptical in shape and cross section. They may be comprised of stainless steel but they may also be comprised of other metal alloys and materials such as aluminum, titanium, nickel-based alloys, ceramic materials, etc. In the embodiment of FIG. 24, middle section 152, first end section 155 and second end section 156 are substantially coaxial over a longitudinal axis.

Figure 25:
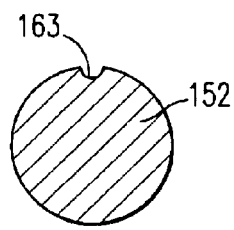
FIG. 25 is a transverse cross sectional view of the shape forming mandrel of FIG. 24 taken at lines 25—25.
Figure 26:
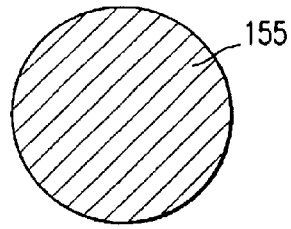
FIG. 26 is a transverse cross. sectional view of the shape forming mandrel of FIG. 24 taken at lines 26—26.

A pressure line recess 163 in the form of a longitudinal channel is formed in the outer surface 151 of the middle section 152 which is configured to accept a pressure line (not shown). The longitudinal channel or pressure line recess 163 is typically semicircular or c-shaped in transverse cross section as shown in FIG. 25 and has a radius of curvature ranging from about 0.005 to about 0.090 inch. The pressure line recess 163 extends along the middle section 152 of mandrel 150 and terminates at first and second end sections 155 and 156. Alternate embodiments of the present invention include a pressure line recess 163 that extends along the first or second end sections 155 and 156.

Figure 27:
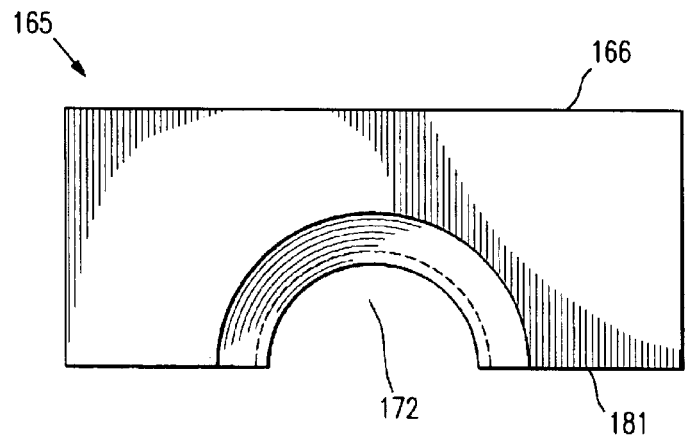
FIG. 27 shows an end view of a mold body portion.
Figure 28:
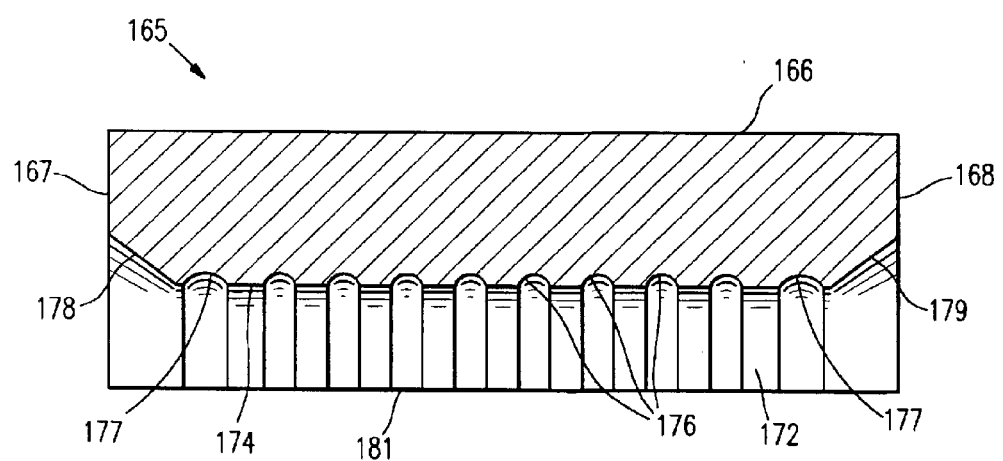
FIG. 28 shows a side view of a longitudinal section of a mold body portion.
Figure 29:
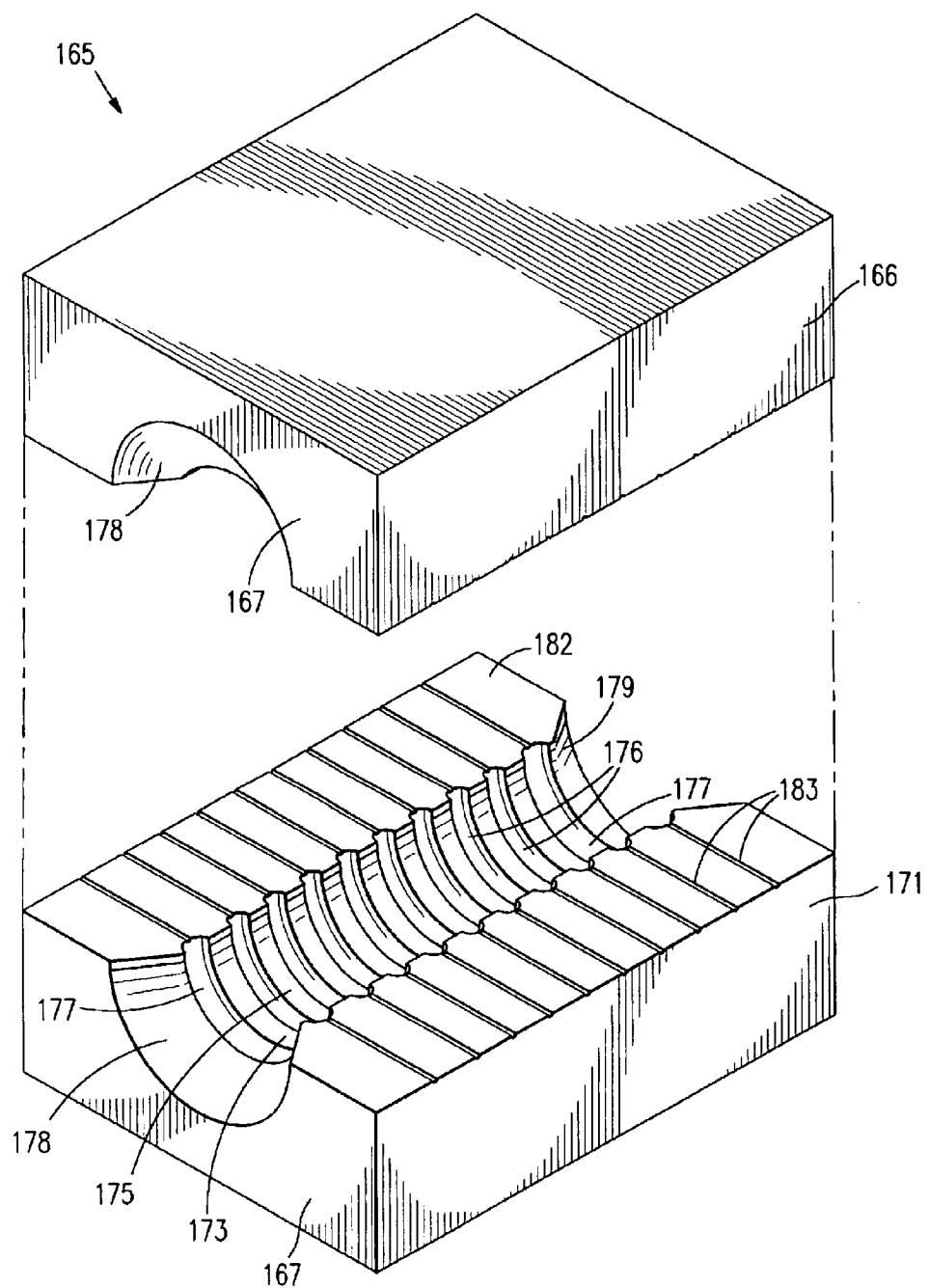
FIG. 29 is a perspective view of a mold body portion separated from another mold body portion.

Referring now to FIGS. 27–29, an outer constraint means in the form of a mold 165 for the manufacture of an endovascular graft, or section thereof, is shown. The mold 165 is configured for the manufacture of a graft section which has at least one inflatable channel or inflatable cuff and can have the same or similar features as the mold 90 shown in FIGS. 16A–16C and 17 above. A first mold body portion 166 has a proximal end 167, a distal end 168 and is configured to mate with a second mold body portion 171 shown in FIG. 29. The first mold body portion 166 and second mold body portion 171 each has a main cavity portion 172 and 173, respectively, formed into the respective mold body portions 166 and 171. Main cavity portions 172 and 173 have inside surface contours 174 and 175, respectively, that are configured to correspond to an outside surface contour of a graft section with the inflatable channels or cuffs in an expanded state. Circumferential channel cavities 176 are disposed on the inside surface contours 174 and 175 of main cavity portions 172 and 173 and are configured to accept circumferential inflatable channels of an endovascular graft or graft section. Circumferential inflatable cuff cavities 177 are disposed on the inside surface contours 174 and 175 of the main cavity portions 172 and 173 near or adjacent a first tapered portion 178 and second tapered portion 179 of the main cavity portions 172 and 173.

First tapered portion 178 of main cavity portions 172 and 173 is disposed adjacent the proximal end 167 of mold 166. Second tapered portion 179 of main cavity portions 172 and 173 is disposed adjacent the distal end 168 of mold as shown in FIG. 28.

First mold body portion 166 has a contact surface 181 that is configured to mate with a contact surface 182 of the second mold body portion 171. The contact surface 182 of the second mold body portion 171 in FIG. 29 has a plurality of exhaust channels 183 formed in the contact surface 182 thereof, extending from main cavity portion 173 to a position outside mold 165. Exhaust channels 183 allow pressurized gas or other material to escape from main cavity portion 172 and 173 of the mold during inflation of the inflatable channels and cuffs. In the embodiment of FIG. 29, exhaust channels 183 are formed, or cut, in contact surface 182 of the second mold body portion 171 only and are configured to longitudinally align with the inflatable cuff cavities 177 and inflatable channel cavities 176 of the main cavity portion 173 of the mold body portion 171, respectively. The longitudinal alignment of exhaust channels 183 with the inflatable channel and cuff cavities 176 and 177 provides for more efficient expansion of the inflatable channels and cuffs. The exhaust channels 183 allow for a greater pressure differential between an inside volume of inflatable cuffs and channels disposed within the cavities 176 and 177 and a volume between an outside surface of the inflatable cuffs and channels and inside surface of the mold 165 during inflation.

The mold 165 shown in FIGS. 27–29 includes two mold body portions 166 and 171; however, other embodiments may include a plurality of mold body portions with at least one of the mold body portions configured to mate with at least one of the other mold body portions to form an assembled mold having a main cavity portion. The main cavity has an inside surface contour that matches an outside surface contour of the endovascular graft, or section thereof, with at least one inflatable channel or cuff of the graft section in an expanded state. Such embodiments may have three, four, five or more mold body portions configured to mate with each other as described above. In some configurations, even a single mold body portion can be used.

With the mold 165 assembled, main cavity portions 172 and 173 typically extends along the length of each mold body portion 166 and 171 and have a length of about 50 to 400 mm, specifically about 100 to about 180 mm. The main cavity portions 172 and 173 typically have an inner transverse dimension of about 3 to 50 mm. Mold body portions 166 and 171 may be comprised of a sintered metal material such as stainless steel or any other suitable material such as aluminum. Exhaust channels 183 may be unnecessary in a mold embodiment made of sintered metal because the porous nature of sintered metal allows gas to escape from any portion of the closed sintered metal mold.

Figure 34:
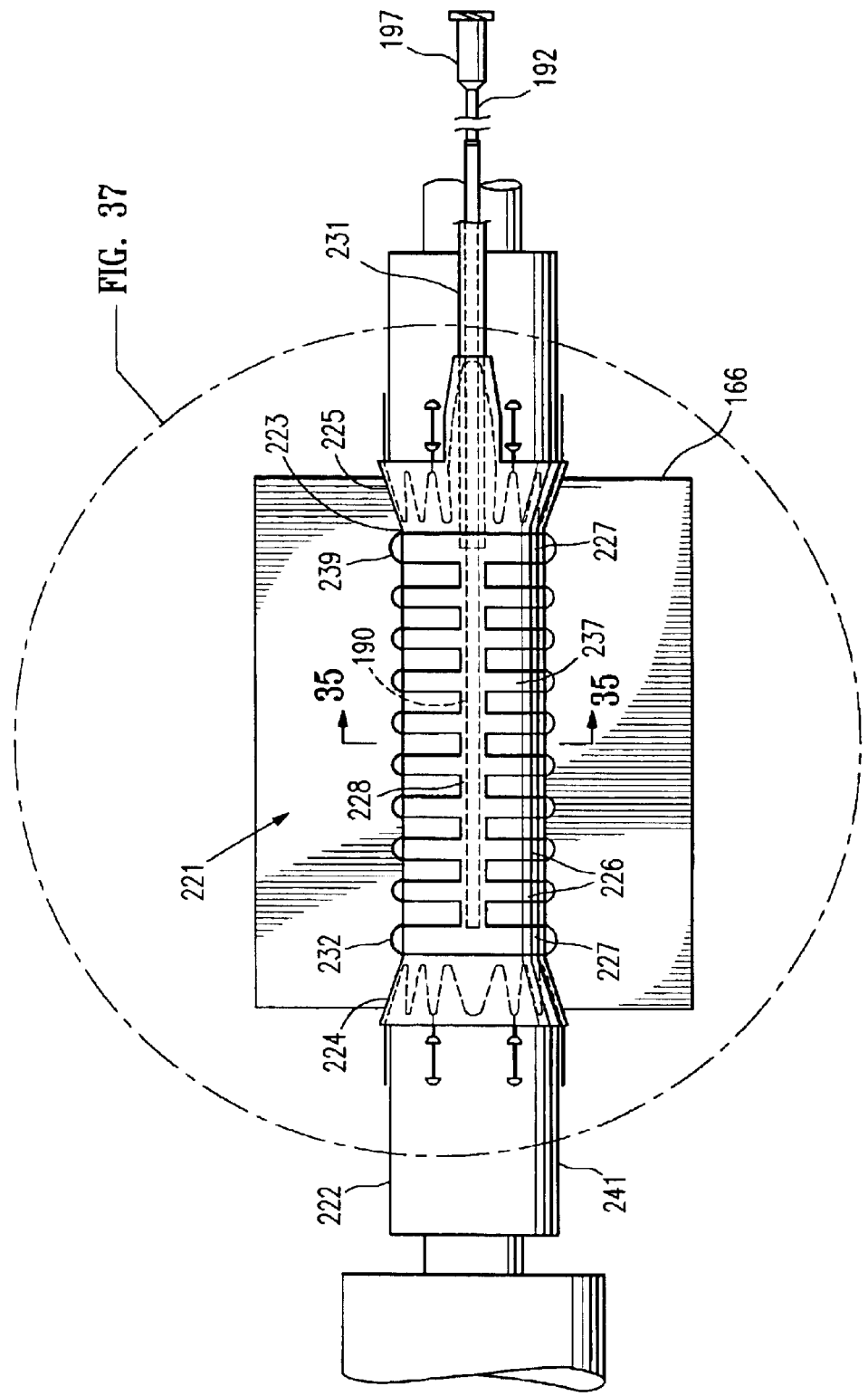
FIG. 34 shows a graft section and shape forming mandrel disposed within a mold cavity portion with one of the mold body portions not shown for clarity of illustration.
Figure 39:
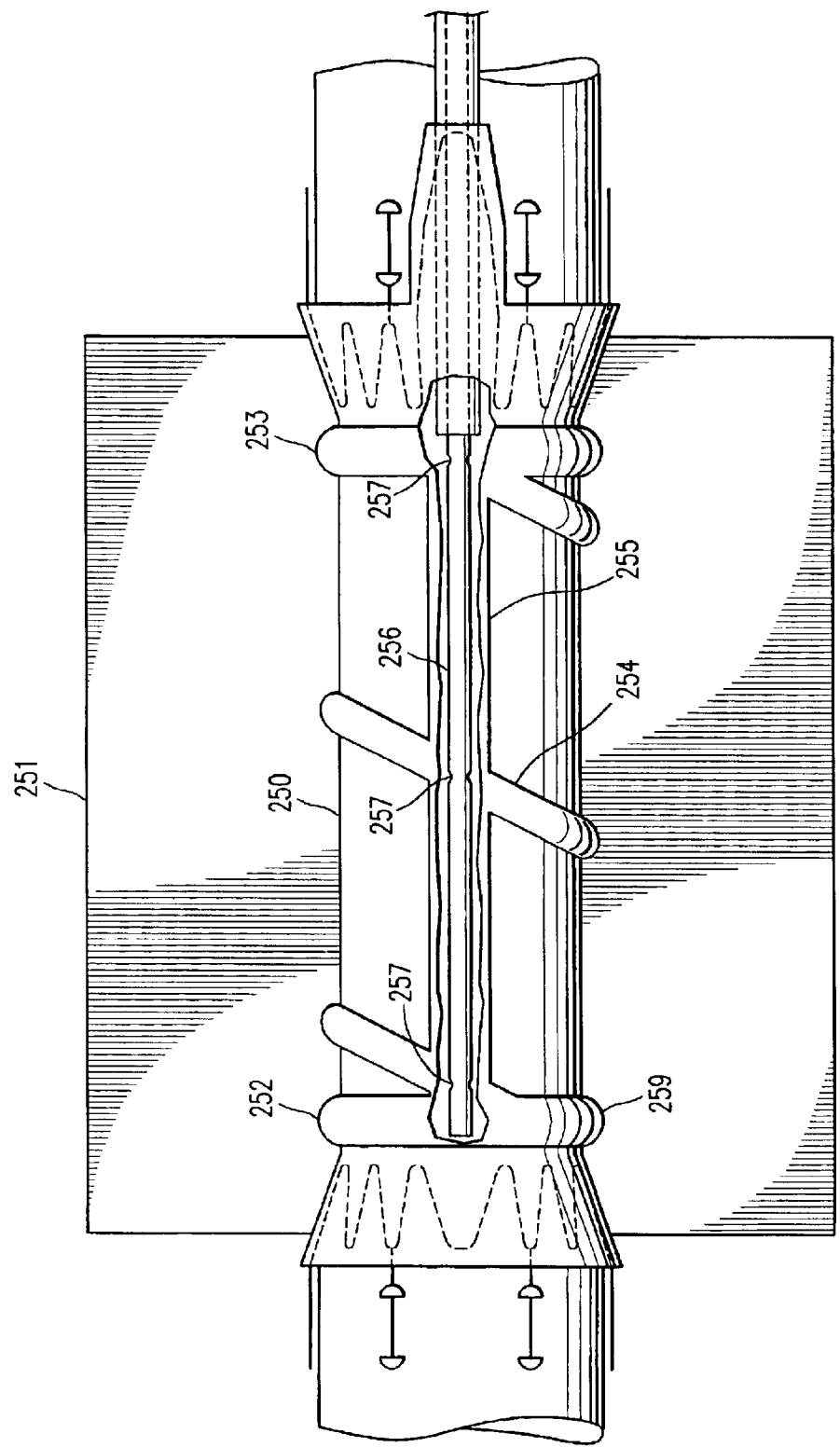
FIG. 39 is a top partial cutaway view of an alternate embodiment of a graft section and shape forming mandrel disposed within a mold cavity portion, with one of the mold body portions not shown for clarity of illustration, showing the pressure line disposed within a temporary expansion channel that is in fluid communication with an expanded helical inflatable channel.

Another embodiment may include a mold body portion having a main cavity portion with at least one longitudinal channel cavity disposed on the inside surface contour of a mold main cavity portion and extending longitudinally along the inside surface contour. The longitudinal channel cavity can have an inside surface contour that corresponds to an outside surface contour of an inflatable longitudinal channel of an endovascular graft as shown in FIG. 34 in an expanded state. Another embodiment may have one or more mold body portions which have at least one helical channel cavity disposed on the inside surface contour of the mold main cavity portion. The helical channel cavity may have an inside surface contour that corresponds to an outside surface contour of an inflatable helical channel of the endovascular graft in an expanded state as shown in FIG. 39.

One of the difficulties encountered in expanding the graft section inflatable channels and cuffs derives from the porosity of the flexible material that may be used for the graft body section. For example, if a porous flexible material such as ePTFE is used for the graft body section, the pressure of pressurized fluid such as a gas injected from an inflation port will decrease with increasing distance from the inflation port as the gas escapes through the porous material. This can result in a graft section with inflatable channels and cuffs which are inconsistently inflated and fixed. FIG. 30 depicts a pressure line 190 for use in the manufacture of an endovascular graft or section thereof which allows for a substantially even distribution of pressure within a network of inflatable channels and cuffs during inflation and fixing of the inflatable channels and cuffs.

The pressure line 190 shown is an elongate gas containment means in the form of an elongate conduit 191 with a length of about 2 to about 12inches. The elongate conduit 191 has a proximal end 192, a distal end 193, a proximal section 194 and a distal section 195. Note the convention used herein where the distal end 193 of conduit 191 will be disposed at the proximal end of graft body section.

A means for producing a permeability gradient in the form of a permeable section 196 is disposed along the conduit distal section 195. Typically disposed at the pressure line proximal end 192 is an adapter or fitting 197 such as a Luer adapter which has an input port 198. Pressurized fluid (gas and/or liquid) may be injected into pressure line 190 through input port 198. The permeable section 196 has a plurality of orifices 201 disposed therein which generally increase in diameter with an increase in distance from the proximal end 192, resulting in a permeability gradient which increases in distance from the conduit proximal end 192. The distal end or extremity 193 of the pressure line 190 can have a distal port (not shown) in addition to the plurality of outlet orifices 201 but may alternately be closed or partially closed.

Proximal section 194 of elongate conduit 191 is typically comprised of stainless steel but may alternately be comprised of materials and metals such as aluminum, titanium, nickel-based alloys, ceramic materials, brass, etc. as well as polymeric tubing such as polyimide. Proximal section 194 generally is cylindrical in transverse cross section as shown in FIG. 31. The proximal section 194 has an angled step down portion 202 with first and second bends 203 and 204 respectively, configured to mate with the mandrel tapered portion 161 or 162 as shown in FIG. 24. Angled step down portion 202 can conform to a tapered configuration of a graft or graft and mandrel assembly in which the pressure line 190 is placed on mandrel 150 during the formation of an endovascular graft body section. Step down portion 202 may be D-shaped in transverse cross section, which allows a more streamlined profile for accommodation of the pressure line 190 within the endovascular graft or graft assembly. Step down portion 202 may form an angle of about 2 to about 30degrees with respect to a longitudinal axis 205 of a distal section of the elongate conduit 191.

Distal to step down portion 202, proximal section 194 is D-shaped in transverse cross section as shown in FIG. 32 and extends toward the distal section 195. The flat portion 206 of the D-shaped cross section allows the pressure line 190 to have a lower profile when lying on a surface such as the outside surface of the tapered portion 161 or 162 of a shape forming mandrel 150.

Distal section 195 has an elongate tubular configuration and is sealingly secured to proximal section 194 at a junction 207. Distal section 195 nominally has a circular transverse cross section and may have an outer transverse dimension of about 0.01 to about 0.1 inch; specifically, about 0.025 to about 0.035 inch. Distal section 195 is formed of a high durometer polymer such as polyimide or the like, although other suitable materials such as stainless steel may be used. The distal section 195 can be D-shaped along a proximal portion 208 thereof when compressed within a distal portion 209 of the proximal section 194 as shown in the transverse cross sectional view of FIG. 32.

The permeable section 196 has a proximal end 211 and a distal end and extends proximally from the distal end 193 of the pressure line 190 for the embodiment shown in FIG. 30. The permeable section 196 has a plurality of outlet orifices 201 which increase in diameter toward the distal end 193 of the pressure line 190. In one embodiment of the pressure line 190, the orifice or orifices 201 of the permeable section 196 have increased area relative to the area of orifices disposed proximally thereof. In such an embodiment, the smallest and most proximal orifices 213 may have a diameter of about 0.002 to about 0.007 inch and the largest orifices 214 adjacent the distal end 212 of the permeable section 196 may have a diameter of about 0.018 to about 0.022 inch. The varied area of the orifices 201 provides for an increase in permeability distally, which results in a predetermined permeability gradient that may be designed or adjusted to alleviate inconsistent expansion of the inflatable channels and cuffs of a graft section. This permeability gradient may increase from about 5 to about 20 percent per centimeter along a direction from the proximal end 211 of permeable section 196 to the distal end 212 of permeable section 196 in some embodiments.

Orifices 201 may be longitudinally spaced along the permeable section 196 so that each opening or orifice 201 corresponds to a given longitudinal spacing and position of circumferential, helical, or other types of inflatable channels or cuffs of an endovascular graft or graft section. Alignment of the orifices 201 with the Inflatable channels or inflatable cuffs of a graft section can provide for a consistent and efficient inflation of the inflatable channels with fluid (liquid or gas) as it travels longitudinally along pressure line 190 and maintains a constant pressure throughout as it fills the inflatable channels and cuffs. In addition, although the embodiment of pressure line 190 of FIG. 30 is shown with a permeable section 196 formed by a plurality of orifices 201, other configurations may be used. For example, permeable section 196 could be made from a porous material such as sintered metal or a porous polymer, wherein the porosity increases over a longitudinal length of the permeable section 196 in order to produce a desired permeability gradient over the length of permeable section 196.

FIG. 34 is a top view of an endovascular graft assembly 221 disposed about an interior surface support means in the form of a shape forming mandrel 222 and disposed within the main cavity portion 172 of first mold body portion 166. The second mold body portion 171 of mold 165 is not shown for the purpose of clarity of illustration. The embodiment of the shape forming mandrel 222 may have the same or similar features to the mandrel 150 shown in FIG. 24. The embodiment of the endovascular graft assembly 221 of FIG. 34 may have the same or similar features to the endovascular graft assembly 105 of FIG. 18 discussed above.

The endovascular graft assembly 221 has a graft body section 223 having a proximal end 224, a distal end 225, and a plurality of circumferential inflatable channels 226 and inflatable cuffs 227 in fluid communication with a longitudinal inflatable channel or spine 228. An inflation port 231 is disposed at the distal end 225 of the graft body section 223 and is in fluid communication with the longitudinal inflatable channel 228. Pressure line 190 is disposed within inflation port 231 and longitudinal inflatable channel 228, with the inflatable channels 226 of the graft body section 223 in an unexpanded or collapsed state. The pressure line 190 extends from the inflation port 231 to a proximal inflatable cuff 232.

Figure 35:
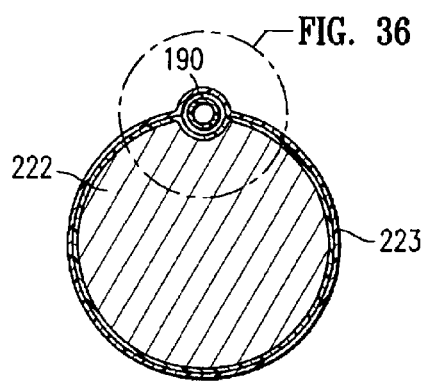
FIG. 35 is a transverse cross sectional view of the graft section, mandrel for shape forming the endovascular graft, and the pressure line embedded within the layers of the fusible material taken at lines 35—35 of FIG. 34.
Figure 36:
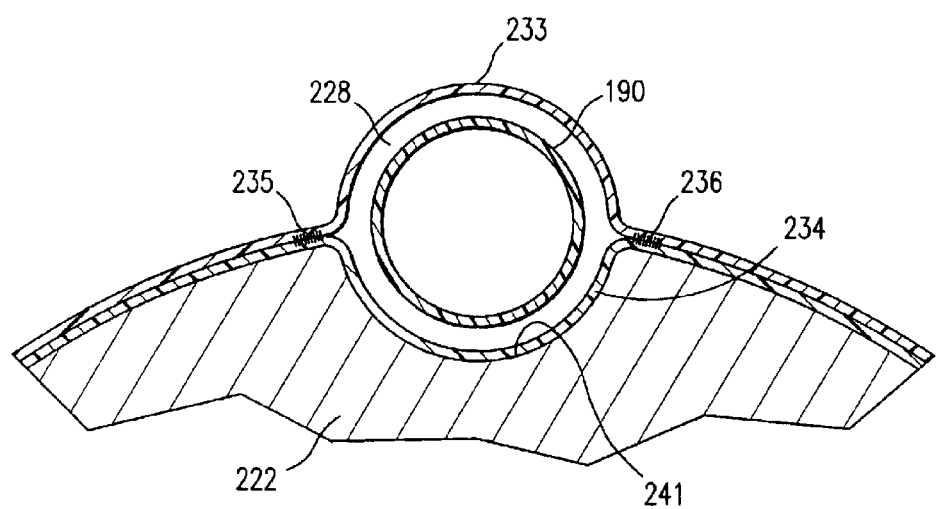
FIG. 36 is an enlarged view showing the pressure line within the layers of fusible material at encircled area 36 of FIG. 35.

FIG. 35 is a transverse cross sectional view of the graft body section 223, mandrel 222 and pressure line 190 and FIG. 36 is an enlarged view of the circled portion of FIG. 35.

Referring to FIG. 36, pressure line 190 is shown disposed within the longitudinal inflatable channel 228, which is disposed between outer layers of flexible material 233 and inner layers of flexible material 234 of graft body section 223. The inner layers of flexible material 234 and outer layers of flexible material 233 are sealed together at a first seam 235 and a second seam 236 which serve to form and define longitudinal inflatable channel 228.

Figure 37:
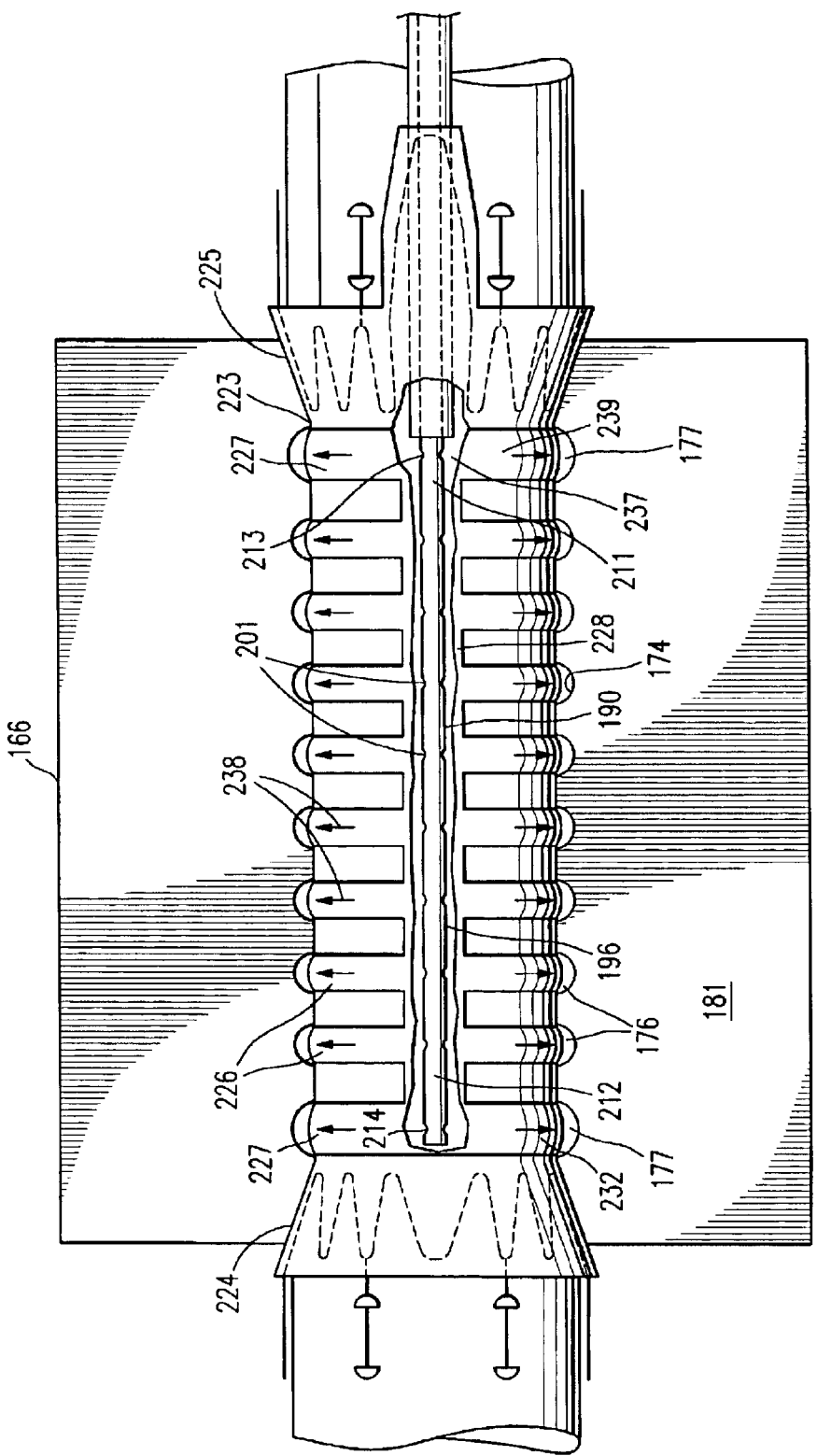
FIG. 37 is a top partial cutaway view of the graft section and shape forming mandrel disposed within a mold cavity portion, with one of the mold body portions not shown for clarity of illustration, showing the pressure line disposed within a longitudinal channel of the graft and a gas being injected into the pressure line of the graft section, expanding the inflatable channels and cuffs.

FIG. 37 is an enlarged view of the circled portion of FIG. 34 with the graft body section 223 partially cut away for the purpose of illustration. Pressure line 190 is positioned such that permeable section 196 of pressure line 190 is disposed within the longitudinal inflatable channel 228 with the outlet orifices 201 aligned with and in fluid communication with the circumferential inflatable channels 226 and circumferential inflatable cuffs 227 of graft body section 223. Additionally, circumferential inflatable channels 226 of the graft, pictured in a noninflated collapsed state, are substantially aligned with and disposed adjacent corresponding circumferential channel cavities 176 of mold body portion 166.

Once pressure line 190 has been properly positioned within the longitudinal inflatable channel 228 of graft body section 223, pressurized fluid, typically a gas, or other material may be injected into the network of inflatable channels and cuffs 237. The injection of pressurized gas into the network of inflatable channels and cuffs 237 forces flexible material 233 of the inflatable channels and cuffs 226 and 227 to expand radially outward as indicated by the arrows 238 in FIG. 37. A more detailed illustration and description of this radial outward expansion of the flexible material 233 may be found in FIG. 17 and its corresponding discussion. The permeability gradient of the permeable section 196 may be chosen so that the pressure and mass flow of pressurized gas exiting the outlet orifice 213 at the permeable section proximal end 211 is substantially the same as the pressure and mass flow of pressurized gas exiting the outlet orifice 214 at the permeable section distal end 212. This ensures that the inflatable cuff 232 at the proximal end 224 of graft body section 223 will have substantially the same amount of inflation as the inflatable cuff 239 at the distal end 225 of graft body section 223.

The pressure gradient may be configured such that the gas pressure at the circumferential inflatable channels 226 (disposed between the inflatable cuffs 227) will receive substantially the same pressure as well. It should be noted that in some embodiments of graft body sections 223, inflatable cuffs 227 may have a larger volume than adjacent inflatable channels 226. Therefore, inflatable cuffs 227 may require more mass flow from a corresponding outlet orifice 201 than the mass flow from an outlet orifice 201 corresponding to a circumferential Inflatable channel 226 in order to maintain the same pressure.

Figure 38:
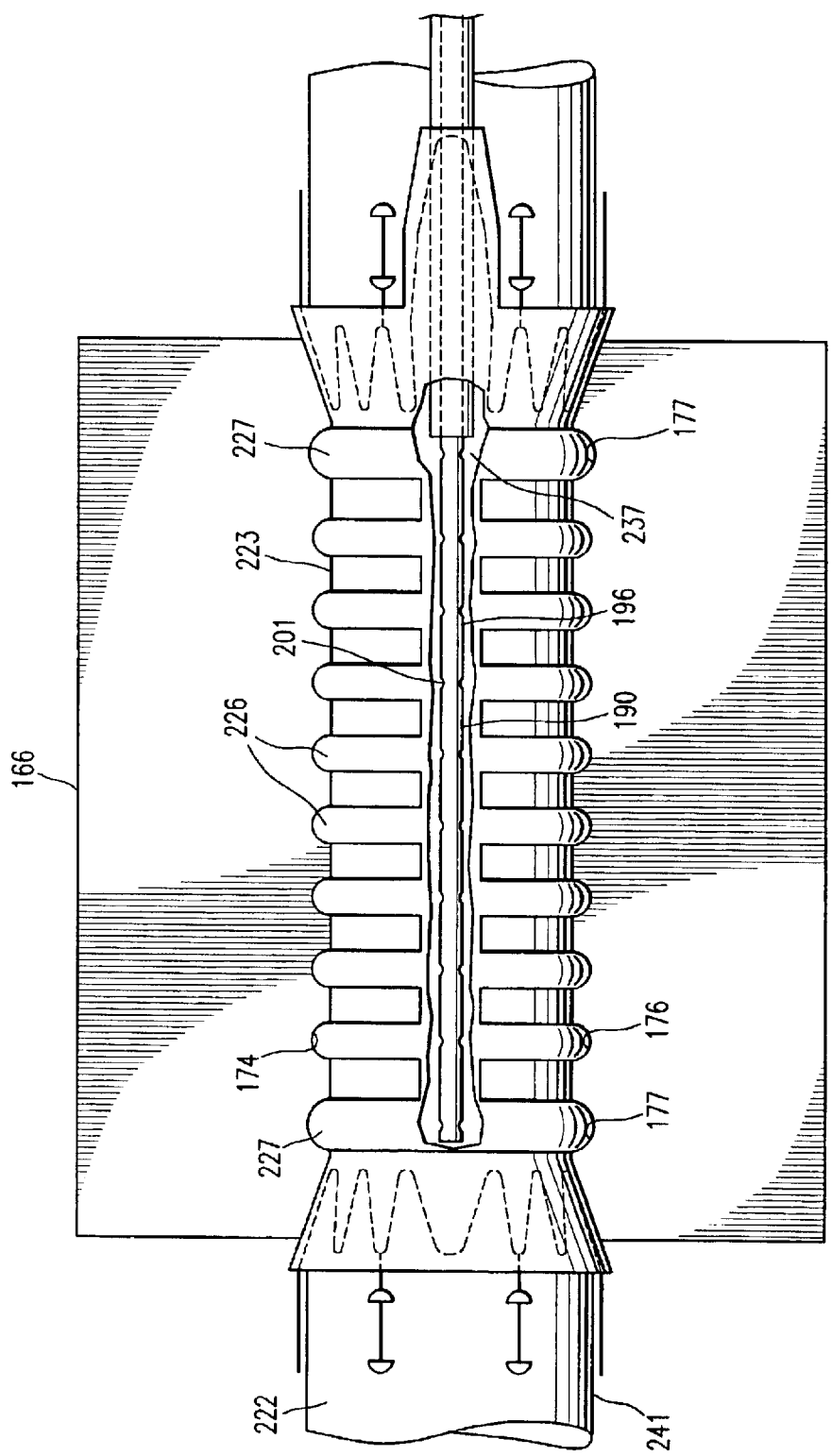
FIG. 38 is a top partial cutaway view of the graft section and shape forming mandrel disposed within a mold cavity portion, with one of the mold body portions not shown for clarity of illustration, showing the pressure line disposed within a longitudinal channel and with the inflatable channels and cuffs in an expanded state.

As the pressurized gas forces the flexible material 233 of the circumferential inflatable channels 226 and inflatable cuffs 227 radially outward, the radial outward movement of the material 233 is ultimately checked by the inside surface contour 174 of the circumferential channel cavities 176 and cuff cavities 177. Inward radial movement or displacement of flexible material 233 is prevented by an outside surface 241 of mandrel 222. FIG. 38 shows the circumferential inflatable channels 226 and inflatable cuffs 227 of graft body section 223 in an expanded state. This allows the circumferential inflatable channels 226 and inflatable cuffs 227 to be formed and then fixed by fixing the flexible material 233 and 234 of the inflatable channels and cuffs 226 and 227 while in an expanded state. As discussed above, if the flexible material is ePTFE, the flexible material may be fixed by a sintering process.

For some non-bifurcated embodiments of graft body sections 223, pressurized gas may be injected at a rate of about 2 to about 15 scfh; specifically, about 5 to about 6 scfh. For such embodiment, the pressure of the pressurized gas can be from about 5 to about 30 psi. For some bifurcated embodiments of graft body sections 223, pressurized gas may injected at a rate of about 15 to about 30 scfh; specifically, about 18 to about 20 scfh. For such bifurcated embodiments, the pressure of the pressurized gas can be from about 15 to about 60 psi. In another embodiment, the rate at which pressurized gas is injected into the inflatable channel and cuff network 237 of the graft body section 223 may be normalized based on the surface area of that portion of endovascular graft body section 223 that is being expanded.

For some graft body section 223 embodiments, there is no permanent longitudinal inflatable channel 228. For these embodiments, it may be desirable to include a temporary longitudinal inflation channel in the graft body section in order to provide access to the inflatable channels of the graft body section for injection of pressurized gas. FIG. 39 shows a graft section 250 disposed within a mold body portion 251 having a proximal inflatable cuff 252, distal inflatable cuff 253, helical inflatable channel 254 and temporary longitudinal inflatable channel 255. The temporary longitudinal inflatable channel 255 is in fluid communication with proximal inflatable cuff 252, distal inflatable cuff 253 and helical inflatable channel 254. A pressure line 256 is disposed within the temporary longitudinal inflatable channel 255 and has outlet orifices 257 that are aligned with and correspond to the proximal inflatable cuff 252, distal inflatable cuff 253 and helical inflatable channel 254. The inflatable channel 254 and cuffs 252 and 253 are shown in an expanded state. Outlet orifices 257 may be configured to produce a pressure gradient that evenly distributes appropriate mass flow from the pressure line 256 to the inflatable cuffs 252 and 253 and inflatable helical channel 254.

Figure 40:
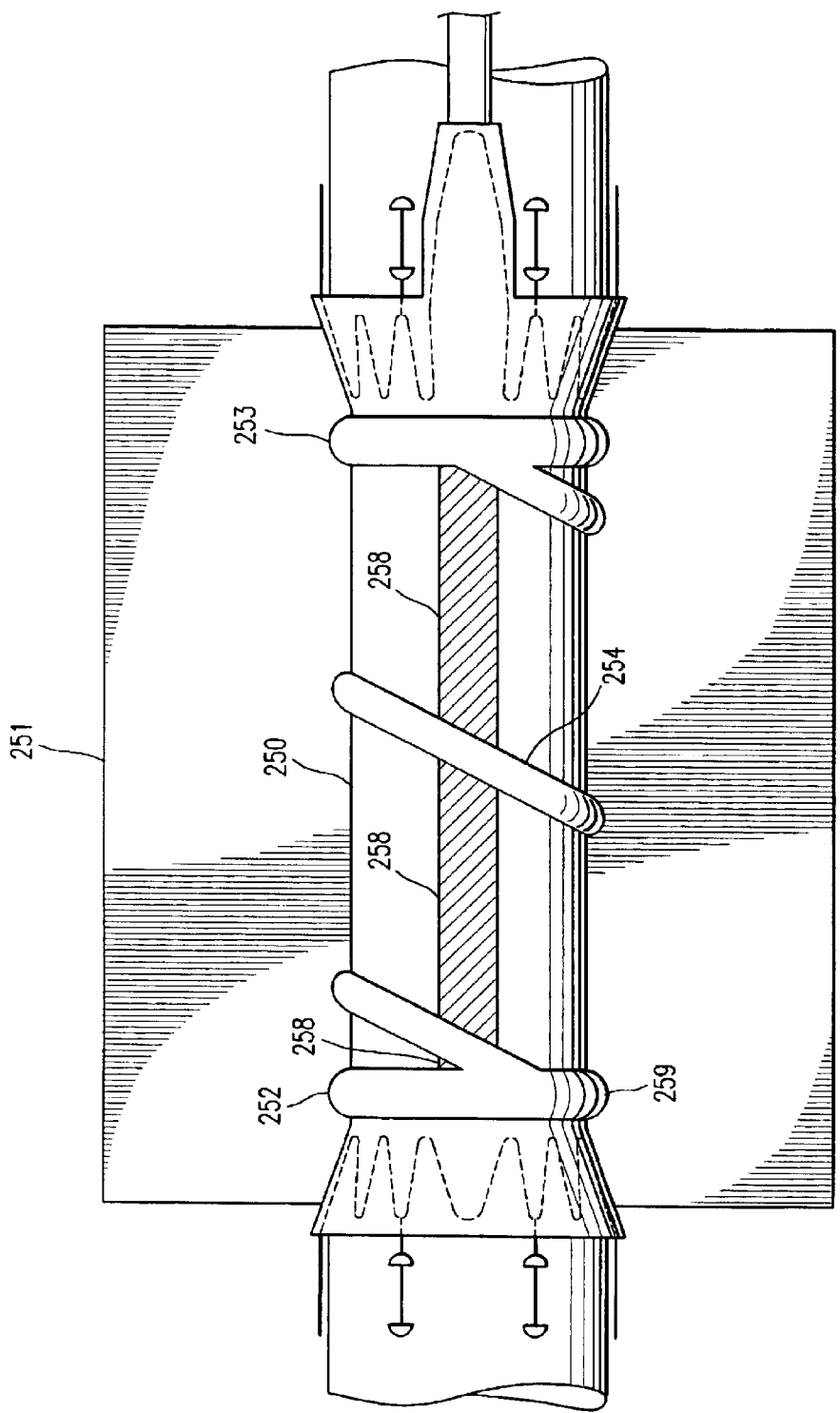
FIG. 40 shows the graft section of FIG. 39 with the temporary expansion channel sealed.

Once the flexible material of the inflatable channel and cuffs 252, 253 and 254 is fixed while the inflatable channel and cuffs 254, 252 and 253 are in the expanded state, pressure line 256 may be removed and the temporary longitudinal inflatable channel 255 sealed in desired portions 258 so as to leave the inflatable cuffs 252 and 253 and inflatable helical channel 254 patent. Sealed portions 258 of the temporary longitudinal inflatable channel 255 shown in FIG. 40 are formed by pressing the layers of flexible material 259 at the sealed portions locations flat together and forming an adhesion by adhesive bonding, thermomechanical sealing or any other suitable method. A suitable material that may be used to seal the sealed portion of the temporary longitudinal inflatable channel 255 is FEP; however, any other suitable material such as silicone elastomer may be used. It may be desirable to use an adhesion method for the sealed portions 258 that maintains a low profile and high degree of flexibility of the sealed portions of the temporary longitudinal inflatable channel 255.

Figure 41:
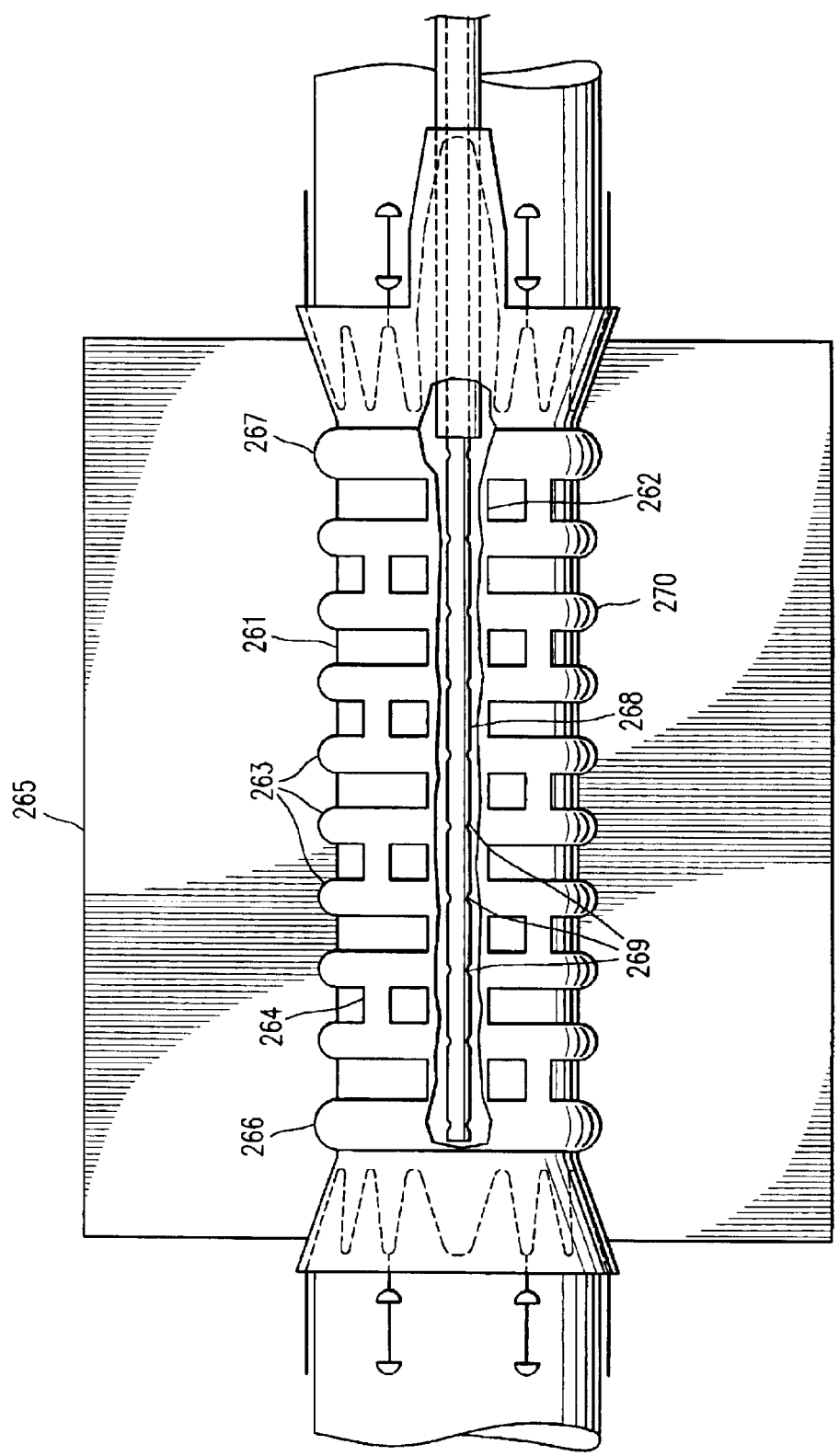
FIG. 41 is a top partial cutaway view of an alternate embodiment of a graft section and shape forming mandrel disposed within a mold cavity portion, with one of the mold body portions not shown for clarity of illustration, with a pressure line disposed within a temporary expansion channel.

FIG. 41 illustrates another embodiment of a graft body section 261 having no permanent longitudinal inflatable channel. A temporary longitudinal inflation channel 262 in the graft section 261 provides access to the circumferential inflatable channels 263 and the longitudinal inflatable channel segments 264 of the graft section 261 for injection of pressurized gas. FIG. 41 shows graft section 261 disposed within a mold body portion 265 and having a proximal inflatable cuff 266, distal inflatable table cuff 267, circumferential inflatable channels 263, longitudinal inflatable channel segments 264 and temporary longitudinal inflatable channel 262. Temporary longitudinal inflatable channel 262 is in fluid communication with the other inflatable cuffs and channels 266, 267, and 263. A pressure line 268 is disposed within the temporary longitudinal inflatable channel 262 and has outlet orifices 269 that are aligned with and correspond to the proximal inflatable cuff 266, distal inflatable cuff 267 and circumferential inflatable channels 263. The inflatable channels 263 and cuffs 266 and 267 are shown in an expanded state. Outlet orifices 269 may be configured to produce a pressure gradient that evenly distributes pressure and appropriate mass flow from pressure line 268 to inflatable cuffs 266 and 267 and inflatable circumferential channels 263.

Figure 42:
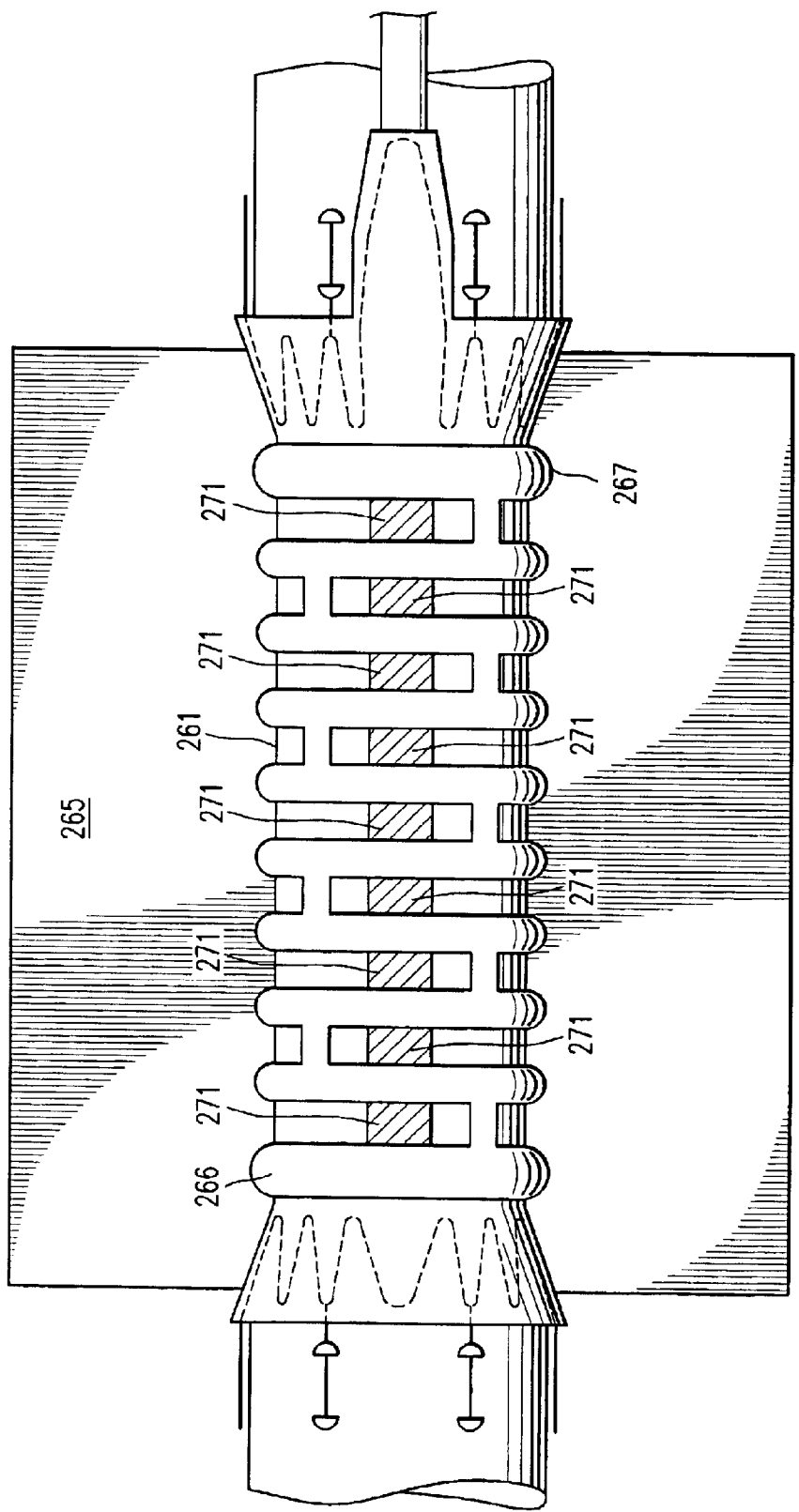
FIG. 42 shows the graft section of FIG. 41 with the temporary expansion channel sealed in selected portions.

Once a flexible material 270 of the inflatable channels 263 and cuffs 266 and 267 are fixed while the inflatable channels 263 and cuffs 266 and 267 are in the expanded state, pressure line 268 may be removed, and the temporary longitudinal inflatable channel 262 may be sealed in desired portions 271 so as to leave the inflatable cuffs 266 and 267 and inflatable channels 263 patent. Sealed portions 271 of temporary longitudinal inflatable channel 262 shown in FIG. 42 may be formed in a manner similar to the sealed portions 258 of the temporary longitudinal inflatable channel 255 of FIG. 40.

While particular forms of embodiments of the invention have been illustrated and described, it will be apparent that various modifications can be made without departing from the spirit and scope of the invention. Accordingly, it is not intended that the invention be limited, except as by the appended claims.

We claim:

1. A mold for the manufacture of an endovascular graft or section thereof which has a plurality of inflatable circumferential channels and at least one inflatable longitudinal channel in fluid communication with and connecting the circumferential channels, the mold comprising:
   a plurality of mold body portions configured to mate with at least one of the other mold body portions to produce an assembled mold having a main cavity portion with an inside surface contour that matches an outside surface contour of the endovascular graft section wherein the assembled mold comprises
   (a) a plurality of circumferential channel cavities that have inside surface contours that match outside surface contours of the plurality of inflatable circumferential channels in an expanded state; and
   (b) at least one longitudinal channel cavity in fluid communication with and connecting the circumferential channel cavities, the longitudinal channel cavity having an inside surface contour that matches an outside surface contour of the at least one inflatable longitudinal channel in an expanded state.

2. The mold of claim 1, further comprising at least one cuff cavity that has an inside surface contour that corresponds to an outside surface contour of an at least one inflatable cuff of the graft section in an expanded state.

3. The mold of claim 1 wherein the mold body portions comprise sintered metal.

4. The mold of claim 1 further comprising at least one exhaust channel in fluid communication with the main cavity portion of the mold and a position outside the mold.

5. The mold of claim 4 wherein the exhaust channel is disposed on a contact surface of a mold body portion.

6. The mold of claim 1 wherein the mold body portions comprise aluminum.

7. The mold of claim 1 wherein the main cavity portion has a length of about 50 to about 300 mm.

8. The mold of claim 1 wherein the main cavity portion has an inner transverse dimension of about 4 to about 50 mm.

9. The mold of claim 1 further comprising a first tapered portion disposed at a first end of the main cavity portion and a second tapered portion disposed at a second end of the main cavity portion, wherein the first and second tapered portions taper to an increased transverse dimension toward respective first and second ends of the mold.

10. A mold for manufacture of an endovascular graft or section thereof which has a plurality of inflatable circumferential channels and at least one inflatable longitudinal channel fluid communication with and connecting the circumferential channels, the mold comprising:
    a first mold body portion and a second mold body portion configured to mate with the first mold body portion to produce an assembled mold having a main cavity portion with an inside surface contour that is configured to correspond to an outside surface contour of the graft section wherein the assembled mold comprises
    (a) a plurality of circumferential channel cavities that have inside surface contours that match outside surface contours of the plurality of inflatable circumferential channels in an expanded state; and
    (b) at least one longitudinal channel cavity in fluid communication with and connecting the circumferential channel cavities, the longitudinal channel cavity having an inside surface contour that matches an outside surface contour of the at least one inflatable longitudinal channel or in an expanded state.

11. The mold of claim 10 further comprising at least one cuff cavity that has an inside surface contour that corresponds to an outside surface contour of an at least one inflatable cuff of the graft section in an expanded state.

12. The mold of claim 10 wherein the mold body portions comprise a sintered metal.

13. The mold of claim 10 further comprising at least one exhaust channel in fluid communication with the main cavity portion and a position outside the mold.

14. The mold of claim 10 wherein the exhaust channel is disposed on a contact surface of the mold body portion.

15. The mold of claim 10 wherein the mold body portions comprise aluminum.

16. The mold of claim 10 wherein the main cavity portion has a length of about 50 to about 300 mm.

17. The mold of claim 10 wherein the main cavity portion has an inner transverse dimension of about 5 to about 50 mm.

18. The mold of claim 10 further comprising a first tapered portion disposed at a first end of the main cavity portion and a second tapered portion disposed at a second end of the main cavity portion.

19. A mold for the manufacture of an endovascular graft or section thereof which has a plurality of inflatable circumferential channels and at least one inflatable helical channel in fluid communication with the circumferential channels, comprising:
    a plurality of mold body portions configured to mate with at least one of the other mold body portions to produce an assembled mold having a main cavity portion with an inside surface contour that matches an outside surface contour of the endovascular graft section, wherein the assembled mold comprises (a) a plurality of circumferential channel cavities that have inside surface contours that match outside surface contours of the plurality of inflatable circumferential channels in an expanded state; and (b) at least one helical channel cavity in fluid communication with the circumferential channel cavities, the helical channel cavity having an inside surface contour that matches an outside surface contour of the at least one inflatable helical channel in an expanded state.

20. The mold of claim 19, further comprising at least one cuff cavity that has an inside surface contour that corresponds to an outside surface contour of an at least one inflatable cuff of the graft section in an expanded state.

21. The mold of claim 19, further comprising at least one exhaust channel in fluid communication with the main cavity portion of the mold and a position outside the mold.

22. The mold of claim 19, further comprising a first tapered portion disposed at a first end of the main cavity portion and a second tapered portion disposed at a second end of the main cavity portion, wherein the first and second tapered portions taper to an increased transverse dimension toward respective first and second ends of the mold.

23. A mold for the manufacture of an endovascular graft or section thereof which has a plurality of inflatable circumferential channels and at least one inflatable helical channel in fluid communication with the circumferential channels, comprising:

a first mold body portion and a second mold body portion configured to mate with the first mold body portion to produce an assembled mold having a main cavity portion with an inside surface contour that is configured to correspond to an outside surface contour of the graft section, wherein the assembled mold comprises (a) a plurality of circumferential channel cavities that have inside surface contours that match outside surface contours of the plurality of inflatable circumferential channels in an expanded state; and (b) at least one helical channel cavity in fluid communication with the circumferential channel cavities, the helical channel cavity having an inside surface contour that matches an outside surface contour of the at least one inflatable helical channel in an expanded state.

24. The mold of claim 23, further comprising at least one cuff cavity that has an inside surface contour that corresponds to an outside surface contour of an at least one inflatable cuff of the graft section in an expanded state.

25. The mold of claim 23, further comprising at least one exhaust channel in fluid communication with the main cavity portion of the mold and a position outside the mold.

26. The mold of claim 23, further comprising a first tapered portion disposed at a first end of the main cavity portion and a second tapered portion disposed at a second end of the main portion, wherein the first and second tapered portions taper to an increased transverse dimension toward respective first and second ends of the mold.

* * * * *